(12) United States Patent
 Taylor et al.

(10) Patent No.: US 10,463,407 B2
(45) Date of Patent: **\*Nov. 5, 2019**

(54) FUSION IMPLANT

(71) Applicant: Wright Medical Technology, Inc., Memphis, TN (US)

(72) Inventors: Alan G. Taylor, Memphis, TN (US); Rebecca Hawkins Wahl, Escondido, CA (US); Bruce R. Lawrence, Oceanside, CA (US)

(73) Assignee: WRIGHT MEDICAL TECHNOLOGY, INC., Memphis, TN (US)

( \* ) Notice: Subject to any disclaimer, the term of this patent is extended or adjusted under 35 U.S.C. 154(b) by 8 days.

This patent is subject to a terminal disclaimer.

(21) Appl. No.: 15/386,686

(22) Filed: Dec. 21, 2016

(65) Prior Publication Data

US 2017/0100172 A1 Apr. 13, 2017

Related U.S. Application Data

(63) Continuation of application No. 14/108,687, filed on Dec. 17, 2013, now Pat. No. 9,554,914, which is a
(Continued)

(51) Int. Cl.
 *A61F 2/42* (2006.01)
 *A61B 17/72* (2006.01)
(Continued)

(52) U.S. Cl.
 CPC ........ *A61B 17/7291* (2013.01); *A61B 17/846* (2013.01); *A61F 2/42* (2013.01);
(Continued)

(58) Field of Classification Search
 CPC ............... A61F 2/42; A61F 2002/4223; A61F 2002/4228–2002/4238;
(Continued)

(56) References Cited

U.S. PATENT DOCUMENTS 5,298,254 A \* 3/1994 Prewett ................ A61B 17/686
 424/422
5,484,443 A \* 1/1996 Pascarella ........... A61F 2/30728
 606/86 R
(Continued)

FOREIGN PATENT DOCUMENTS

WO WO 2011/110784 A1 9/2011

*Primary Examiner* — Alvin J Stewart
(74) *Attorney, Agent, or Firm* — Duane Morris LLP

(57) ABSTRACT

An implant that facilitates the fusion of a first bone part with a second bone part includes an implant body that extends between the first bone part and the second bone part. The implant body includes a first portion that fits within a first receiving aperture in the first bone part, and the implant body includes a second portion that fits within a second receiving aperture in the second bone part. At least one of the first portion and the second portion can be made of bone. Additionally, at least the second portion is formed to have a non-circular cross-sectional shape to inhibit relative motion between the bone parts and the implant body.

10 Claims, 18 Drawing Sheets

Related U.S. Application Data continuation-in-part of application No. 13/409,333, filed on Mar. 1, 2012, now abandoned.

(60) Provisional application No. 61/599,335, filed on Feb. 15, 2012, provisional application No. 61/569,421, filed on Dec. 12, 2011.

(51) Int. Cl.
    *A61B 17/84* (2006.01)
    *A61F 2/30* (2006.01)
    *A61B 17/86* (2006.01)

(52) U.S. Cl.
    CPC .......... *A61B 17/7283* (2013.01); *A61B 17/86* (2013.01); *A61F 2/4225* (2013.01); *A61F 2/4241* (2013.01); *A61F 2/4261* (2013.01); *A61F 2002/30154* (2013.01); *A61F 2002/30265* (2013.01); *A61F 2002/30622* (2013.01); *A61F 2002/30879* (2013.01); *A61F 2002/30892* (2013.01); *A61F 2002/30904* (2013.01)

(58) Field of Classification Search
    CPC ............... A61F 2002/4243–2002/4258; A61F 2002/4264–2002/4297; A61F 2/4241; A61B 17/7291; A61B 17/72
    See application file for complete search history.

(56) References Cited

U.S. PATENT DOCUMENTS

| | | | |
|---|---|---|---|
| 6,294,187 B1 | 9/2001 | Boyce et al. | |
| 6,440,444 B2 | 8/2002 | Boyce et al. | |
| 6,443,987 B1* | 9/2002 | Bryan | A61B 17/025 623/17.11 |
| 6,660,008 B1* | 12/2003 | Foerster | A61B 17/0401 411/34 |
| 6,926,737 B2 | 8/2005 | Jackson | |
| 7,662,184 B2* | 2/2010 | Edwards | A61L 27/3608 623/17.11 |
| 8,262,712 B2* | 9/2012 | Coilard-Lavirotte | A61B 17/1604 606/300 |
| 8,834,572 B2* | 9/2014 | Averous | A61F 2/42 623/16.11 |
| 8,840,677 B2* | 9/2014 | Kale | A61B 17/686 606/313 |
| D720,072 S * | 12/2014 | Cheney | A61F 2/42 D24/155 |
| 9,044,287 B2* | 6/2015 | Reed | A61B 17/7291 |
| 9,072,564 B2* | 7/2015 | Reed | A61B 17/7291 |
| 9,161,789 B2* | 10/2015 | Peyrot | A61F 2/30 |
| 9,168,074 B2* | 10/2015 | Prandi | A61B 17/68 |
| D745,163 S * | 12/2015 | Cheney | D24/155 |
| 9,282,977 B2* | 3/2016 | Penzimer | A61B 17/8875 |
| 9,474,561 B2* | 10/2016 | Shemwell | A61B 17/7291 |
| 9,517,098 B2* | 12/2016 | Anderson | A61B 17/8872 |
| 9,522,022 B2* | 12/2016 | Cheney | A61B 17/7266 |
| 9,545,274 B2* | 1/2017 | McCormick | A61B 17/7291 |
| 9,554,914 B2* | 1/2017 | Taylor | A61F 2/42 |
| 9,675,392 B2* | 6/2017 | Shemwell | A61B 17/7291 |
| 9,724,138 B2* | 8/2017 | Palmer | A61B 17/7266 |
| 9,724,139 B2* | 8/2017 | McCormick | A61B 17/7291 |
| 9,724,140 B2* | 8/2017 | McCormick | A61B 17/8883 |
| 9,757,168 B2* | 9/2017 | Seavey | A61B 17/7291 |
| 9,775,659 B2* | 10/2017 | Cheney | A61B 17/8872 |
| 9,808,296 B2* | 11/2017 | McCormick | A61B 17/1604 |
| 2001/0043940 A1 | 11/2001 | Boyce et al. | |
| 2002/0029084 A1* | 3/2002 | Paul | A61F 2/28 623/23.63 |
| 2005/0216012 A1* | 9/2005 | Willmen | A61B 17/686 606/323 |
| 2006/0036322 A1 | 2/2006 | Reiley | |
| 2006/0074421 A1* | 4/2006 | Bickley | A61B 17/686 606/290 |
| 2006/0190088 A1* | 8/2006 | Parks | A61B 17/562 623/21.11 |
| 2006/0293748 A1* | 12/2006 | Alexander | A61F 2/447 623/17.11 |
| 2007/0038219 A1* | 2/2007 | Matthis | A61B 17/864 623/17.11 |
| 2007/0067034 A1* | 3/2007 | Chirico | A61B 17/70 623/17.11 |
| 2008/0132894 A1* | 6/2008 | Coilard-Lavirotte | A61B 17/1604 606/60 |
| 2008/0161864 A1* | 7/2008 | Beck | A61F 2/0811 606/326 |
| 2008/0177262 A1* | 7/2008 | Augoyard | A61B 17/68 606/70 |
| 2008/0221623 A1* | 9/2008 | Gooch | A61B 17/686 606/302 |
| 2010/0057208 A1* | 3/2010 | Dryer | A61F 2/446 623/17.16 |
| 2010/0131014 A1* | 5/2010 | Peyrot | A61F 2/30 606/300 |
| 2010/0168798 A1* | 7/2010 | Clineff | A61L 27/54 606/279 |
| 2011/0082561 A1* | 4/2011 | Forrester | A61F 2/4225 623/21.19 |
| 2011/0144766 A1* | 6/2011 | Kale | A61B 17/686 623/23.63 |
| 2011/0301652 A1* | 12/2011 | Reed | A61B 17/7291 606/319 |
| 2011/0301653 A1* | 12/2011 | Reed | A61B 17/1604 606/319 |
| 2012/0089197 A1* | 4/2012 | Anderson | A61B 17/7233 606/310 |
| 2013/0066383 A1* | 3/2013 | Anderson | A61B 17/7233 606/329 |
| 2013/0123862 A1* | 5/2013 | Anderson | A61B 17/88 606/321 |
| 2013/0131822 A1* | 5/2013 | Lewis | A61F 2/4606 623/21.19 |
| 2013/0150965 A1 | 6/2013 | Taylor et al. | |
| 2014/0052196 A1* | 2/2014 | McGinley | A61B 17/8605 606/319 |
| 2014/0142715 A1* | 5/2014 | McCormick | A61B 17/8883 623/21.19 |
| 2014/0309747 A1* | 10/2014 | Taylor | A61F 2/42 623/21.11 |
| 2015/0073413 A1* | 3/2015 | Palmer | A61B 17/7266 606/63 |
| 2015/0142066 A1* | 5/2015 | Shemwell | A61B 17/7291 606/301 |
| 2015/0374503 A1* | 12/2015 | Lovick | A61B 17/7291 623/23.5 |
| 2016/0015437 A1* | 1/2016 | Elleby | A61B 17/7291 606/329 |
| 2016/0045324 A1* | 2/2016 | Austin | A61B 17/7291 623/21.19 |
| 2016/0081728 A1* | 3/2016 | McCormick | A61B 17/1604 606/64 |
| 2016/0256290 A1* | 9/2016 | Seavey | A61B 17/7291 |
| 2016/0338747 A1* | 11/2016 | Shemwell | A61B 17/7233 |
| 2017/0000618 A1* | 1/2017 | Tyber | A61F 2/4225 |
| 2017/0007416 A1* | 1/2017 | Sander | A61F 2/4225 |
| 2017/0035473 A1* | 2/2017 | Shemwell | A61B 17/7291 |
| 2017/0100172 A1* | 4/2017 | Taylor | A61F 2/42 |
| 2017/0151061 A1* | 6/2017 | Lavi | A61F 2/4225 |
| 2017/0156766 A1* | 6/2017 | Anderson | A61B 17/7233 |
| 2017/0156876 A1* | 6/2017 | Viladot Perice | A61F 2/4202 |
| 2017/0239059 A1* | 8/2017 | Boublil | A61F 2/4225 |
| 2017/0319349 A1* | 11/2017 | Kowalczyk | A61B 17/7291 |
| 2017/0333081 A1* | 11/2017 | Cordier | A61B 17/68 |
| 2018/0021145 A1* | 1/2018 | Seavey | A61F 2/4225 438/419 |

(56) References Cited

U.S. PATENT DOCUMENTS

2018/0049881 A1\* 2/2018 Austin ................. A61B 17/866
2018/0140338 A1\* 5/2018 Wingenfeld ....... A61B 17/7258
2018/0168703 A1\* 6/2018 Roman .............. A61B 17/7291

\* cited by examiner

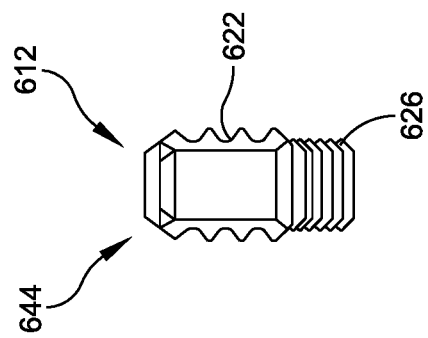
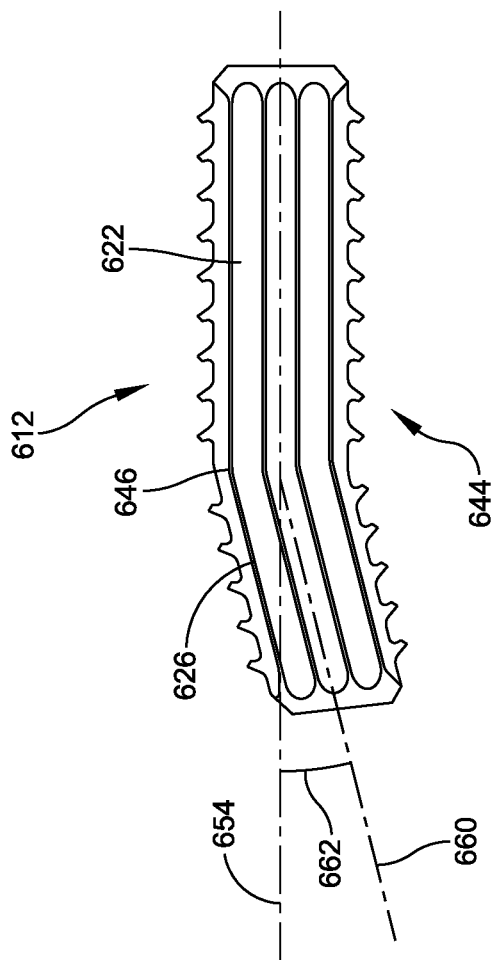

| SIZE | LENGTH |
|------|--------|
| 10 | 10 |
| 12 | 12 |
| 14 | 14 |
| 16 | 16 |
| 18 | 18 |

FUSION IMPLANT

CROSS REFERENCE TO RELATED APPLICATIONS

This application is a continuation of U.S. patent application Ser. No. 14/108,687, filed Dec. 17, 2013, which is a continuation-in-part of non-provisional U.S. application Ser. No. 13/409,333, filed Mar. 1, 2012, and entitled "Fusion Implant" which claims priority of U.S. Provisional Application Ser. No. 61/569,421 filed on Dec. 12, 2011, entitled "Fusion Implant"; and on U.S. Provisional Application Ser. No. 61/599,335 filed on Feb. 15, 2012, entitled "Fusion Implant." As far as is permitted, the contents of U.S. Provisional Application Ser. No. 61/569,421; and U.S. Provisional Application Ser. No. 61/599,335 are incorporated herein by reference.

BACKGROUND

It is well known that some people have problems with one or more joints in their body, including in their feet and/or hands, and/or with the healing of broken bones. For example, many people suffer from potentially painful conditions with their toes, such as claw toe, mallet toe, hammer toe, or curly toe. Several procedures have been developed to treat these and other conditions and/or to treat and encourage the proper healing of broken bones. However, existing treatments are not entirely satisfactory.

SUMMARY

The present invention is directed to an implant that facilitates the fusion of a first bone part with a second bone part. The first bone part includes a first receiving aperture and the second bone part includes a second receiving aperture. In certain embodiments, the implant comprises an implant body that extends between the first bone part and the second bone part. Additionally, the implant body includes a first portion that fits within the first receiving aperture in the first bone part. Further, the implant body includes a second portion that fits within the second receiving aperture in the second bone part. In some embodiments, at least one of the first portion and the second portion is made of bone. Additionally, in such embodiments, at least one of the first portion and the second portion is formed to have a non-circular cross-sectional shape to inhibit relative motion between the bone parts and the implant body.

In one embodiment, at least one of the first portion and the second portion has a generally rectangular cross-sectional shape. Additionally and/or alternatively, in one embodiment, at least one of the first portion and the second portion has a generally octagonal cross-sectional shape.

Additionally, in certain embodiments, each of the first portion and the second portion are made of bone. In one embodiment, at least one of the first portion and the second portion is made of cortical bone. Further, in one embodiment, at least one of the first portion and the second portion is made of bone that is partially demineralized.

Further, in one embodiment, each of the first portion and the second portion are formed to have a non-circular cross-sectional shape to inhibit relative motion between the bone parts and the implant body. Alternatively, in one embodiment, one of the first portion and the second portion is threaded and includes a substantially circular cross-section that is threaded into its corresponding receiving aperture.

In some embodiments, the implant body further includes a plurality of ridges. In such embodiments, at least one of the ridges extends substantially transverse to a longitudinal axis of the implant body.

Certain embodiments of the invention also can be used as nail allografts. The implant body can include ridges or teeth that are specifically designed to enable the fusion implant to effectively draw the bone parts together. Further, the implant body can include a plurality of longitudinal grooves or flutes to help insertion of the fusion implant and/or to inhibit relative movement between the first bone part and the second bone part.

In one embodiment, the implant body is generally straight beam shaped. Alternatively, in one embodiment, the second portion is angled relative to the first portion.

Additionally, in certain embodiments, the implant body can include an orientation indicator that indicates that the first portion of the implant body is to be inserted into the first bone part. Moreover, in some embodiments, the implant body can further include a depth indicator that indicates when the first portion is properly inserted into the first bone part. In one such embodiment, the depth indicator includes a joint line feature to indicate an insertion depth of the first portion into the first bone part.

Further, the present invention is directed to a method for fusing a first bone part with a second bone part. In certain embodiments, the method comprises the steps of (i) extending an implant body between the first bone part and the second bone part, the implant body including a first portion and a second portion; (ii) fitting the first portion within a first receiving aperture in the first bone part; and (iii) fitting the second portion within a second receiving aperture in the second bone part, wherein at least one of the first portion and the second portion is made of bone, and wherein at least one of the first portion and the second portion is formed to have a non-circular cross-sectional shape to inhibit relative motion between the bone parts and the implant body.

BRIEF DESCRIPTION OF THE DRAWING

The novel features of this invention, as well as the invention itself, both as to its structure and its operation, will be best understood from the accompanying drawings, taken in conjunction with the accompanying description, in which similar reference characters refer to similar parts, and in which:

FIG. 6A is a side view of still another embodiment of a fusion implant having features of the present invention;

FIG. 6B is an end view of the fusion implant illustrated in FIG. 6A;

DESCRIPTION

The present invention is directed to a fusion implant that can be used to treat and fuse two bone parts. As non-exclusive examples, the fusion implant can be used to assist in the fusion of articular joints in the forearm, wrist, hand (including fingers), lower leg, foot (including toes), and/or ankle of a human or animal. In these examples, one side of the joint being fused can be considered a first bone part, and the other side of the joint can be considered a second bone part. Additionally and/or alternatively, the fusion implant can be used in the repair of fractures of various bones in the body of a human or animal including the clavicle, humerus, ulna, radius, tibia or fibula. In these examples, one side of the fractured bone can be considered the first bone part, and the other side of the fractured bone can be considered the second bone part.

As an overview, in certain embodiments, the fusion implant can include an implant body that is made of bone. For example, as provided herein, the implant body can be made from cortical bone. Moreover, the implant body can be made of bone that is partially demineralized. In one specific example, the implant body can be a partially demineralized human cortical bone allograft. Additionally, in certain embodiments, the implant body can be formed to have a non-circular cross-sectional shape to inhibit relative movement/rotation between the bone parts and the implant body. Further, the implant body can include a plurality of ridges that inhibit the implant from being pulled out of the bone, wherein one or more of the ridges extend substantially transverse to a longitudinal axis of the implant body.

Figure 1:
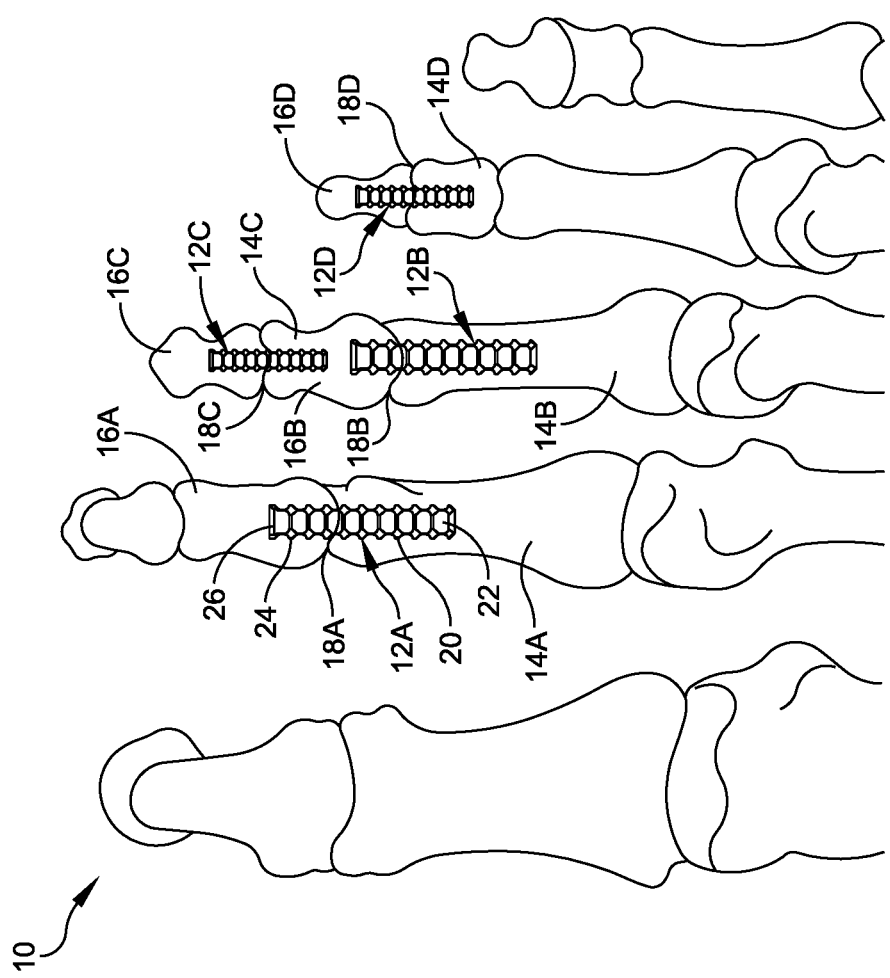
FIG. 1 is a top view of a portion of a foot with four fusion implants having features of the present invention implanted therein.

FIG. 1 is a top view of a portion of a body part 10, e.g., a portion of a right foot in this example, with four fusion implants, i.e. a first fusion implant 12A, a second fusion implant 12B, a third fusion implant 12C and a fourth fusion implant 12D (also referred to herein as an "implant" or "implants") having features of the present invention implanted therein. More particularly, FIG. 1 illustrates (i) the first implant 12A that facilitates the fusion of a first bone part 14A (a proximal phalanx) and a second bone part 16A (a middle phalanx) of a first joint 18A (proximal interphalangeal joint "PIP" of the second toe); (ii) the second implant 12B that facilitates the fusion of a first bone part 14B and a second bone part 16B of a second joint 18B (proximal interphalangeal joint of the third toe); (iii) the third implant 12C that facilitates the fusion of a first bone part 14C (a middle phalanx) and a second bone part 16C (a distal phalanx) of a third joint 18C (distal interphalangeal joint "DIP" of the third toe); and (iv) the fourth implant 12D that facilitates the fusion of a first bone part 14D and a second bone part 16D of a fourth joint 18D (distal interphalangeal joint of the fourth toe).

In this embodiment, prior to the insertion of the implants 12A, 12B, 12C, 12D for each interphalangeal joint 18A, 18B, 18C, 18D, respectively, the proper amount of bone is removed and a first (or proximal) receiving aperture 20 is created in each of the first bone parts 14A, 14B, 14C, 14D that is sized and shaped to receive a first (or proximal) portion 22 of the respective implant 12A, 12B, 12C, 12D. Somewhat similarly, the proper amount of bone is removed and a second (or distal) receiving aperture 24 is created in each of the second bone parts 16A, 16B, 16C, 16D that is sized and shaped to receive a second (or distal) portion 26 of the respective implant 12A, 12B, 12C, 12D. For example, each receiving aperture 20, 24 can have a cross-section that is substantially circle-shaped, triangle-shaped, square-shaped, rectangle-shaped, pentagon-shaped, hexagon-shaped, octagon-shaped, or some other shape. With this design, (i) the first implant 12A is inserted and fitted within the receiving apertures 20, 24 of the bone parts 14A, 18A, respectively, and extends between the bone parts 14A, 18A; (ii) the second implant 12B is inserted and fitted within the receiving apertures 20, 24 of the bone parts 14B and 14C, respectively, and extends between the bone parts 14B, 14C; (iii) the third implant 12C is inserted and fitted within the receiving apertures 20, 24 of the bone parts 14C and 16C, respectively, and extends between the bone parts 14C, 16C; and (iv) the fourth implant 12D is inserted and fitted within the receiving apertures 20, 24 of the bone parts 14D, 16D, respectively, and extends between the bone parts 14D, 16D.

In one embodiment, the articular joint surface of the bone parts 14A-14D, 16A-16D will be prepped by removing the damaged cartilage and then creating a hole through both opposing joint surfaces (proximal and distal) of the bone parts 14A-14D, 16A-16D. The design of the implant 12A-12D is such that the machined surface of the implant 12A-12D prevents the two opposing bone parts 14A-14D, 16A-16D from moving in translation, distraction, or rotation relative to each other. The surface shape of the implant 12A-12D also optimizes the surface area of the implant 12A-12D interfacing with the prepared bone parts 14A-14D, 16A-16D receiving the implant 12A-12D.

Figure 2:
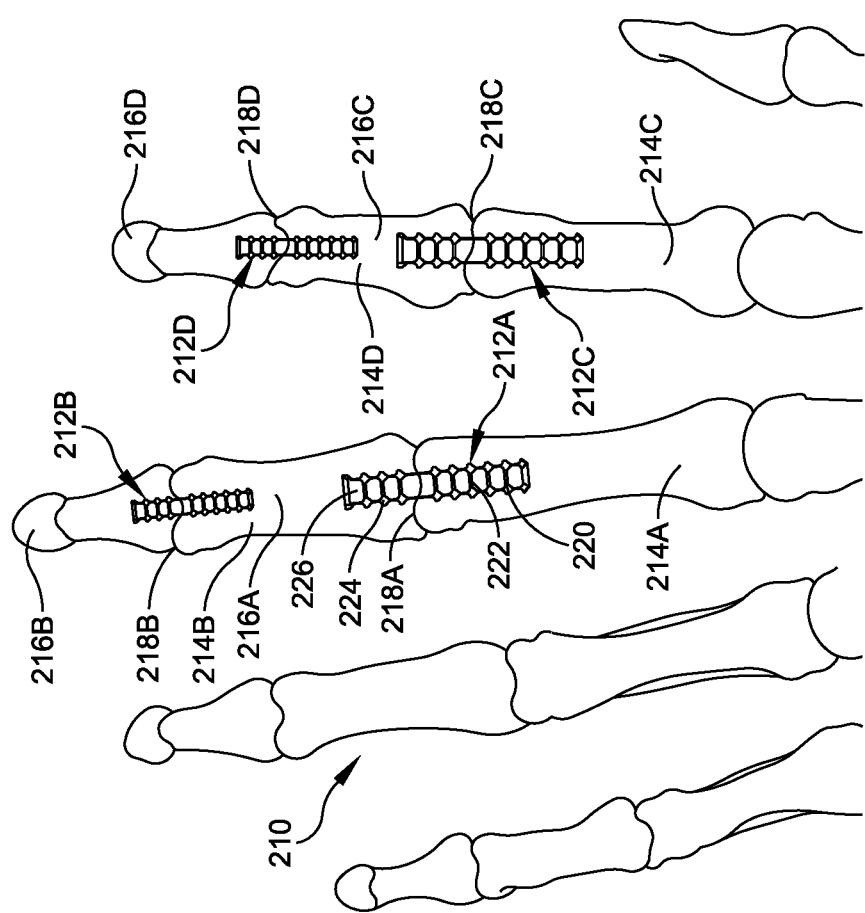
FIG. 2 is a top view of a portion of a hand with four fusion implants having features of the present invention implanted therein.

FIG. 2 is a top view of a portion of a body part 210, e.g., a portion of a left hand in this example, with four fusion implants, i.e. a first fusion implant 212A, a second fusion implant 212B, a third fusion implant 212C and a fourth fusion implant 212D (also referred to herein as an "implant" or "implants") having features of the present invention implanted therein. More particularly, FIG. 2 illustrates (i) the first implant 212A that facilitates the fusion of a first bone part 214A and a second bone part 216A of a first joint 218A (proximal interphalangeal joint of the middle finger); (ii) the second implant 212B that facilitates the fusion of a first bone part 214B and a second bone part 216B of a second joint 218B (distal interphalangeal joint of the middle finger); (iii) the third implant 212C that facilitates the fusion of a first bone part 214C and a second bone part 216C of a third joint 218C (proximal interphalangeal joint of the index finger); and (iv) the fourth implant 212D that facilitates the fusion of a first bone part 214D and a second bone part 216D of a fourth joint 218D (distal interphalangeal joint of the index finger).

Similar to the embodiment illustrated in FIG. 1, in this embodiment, prior to the insertion of the implants 212A, 212B, 212C, 212D for each interphalangeal joint 218A, 218B, 218C, 218D, respectively, the proper amount of bone is removed and a first (or proximal) receiving aperture 220 is created in each of the first bone parts 214A, 214B, 214C, 214D that is sized and shaped to receive a first (or proximal) portion 222 of the respective implant 212A, 212B, 212C, 212D. Somewhat similarly, the proper amount of bone is removed and a second (or distal) receiving aperture 224 is created in each of the second bone parts 216A, 216B, 216C, 216D that is sized and shaped to receive a second (or distal) portion 226 of the respective implant 212A, 212B, 212C, 212D. For example, each receiving aperture 220, 224 can have a cross-section that is substantially circle-shaped, triangle-shaped, square-shaped, rectangle-shaped, pentagon-shaped, hexagon-shaped, octagon-shaped, or some other shape. With this design, (i) the first implant 212A is inserted and fitted within the receiving apertures 220, 224 of the bone parts 214A, 216A, respectively, and extends between the bone parts 214A, 216A; (ii) the second implant 212B is inserted and fitted within the receiving apertures 220, 224 of the bone parts 214B, 216B, respectively, and extends between the bone parts 214B, 216B; (iii) the third implant 212C is inserted and fitted within the receiving apertures 220, 224 of the bone parts 214C, 216C, respectively, and extends between the bone parts 214C, 216C; and (iv) the fourth implant 212D is inserted and fitted within the receiving apertures 220, 224 of the bone parts 214D, 216D, respectively, and extends between the bone parts 214D, 216D.

Figure 3:
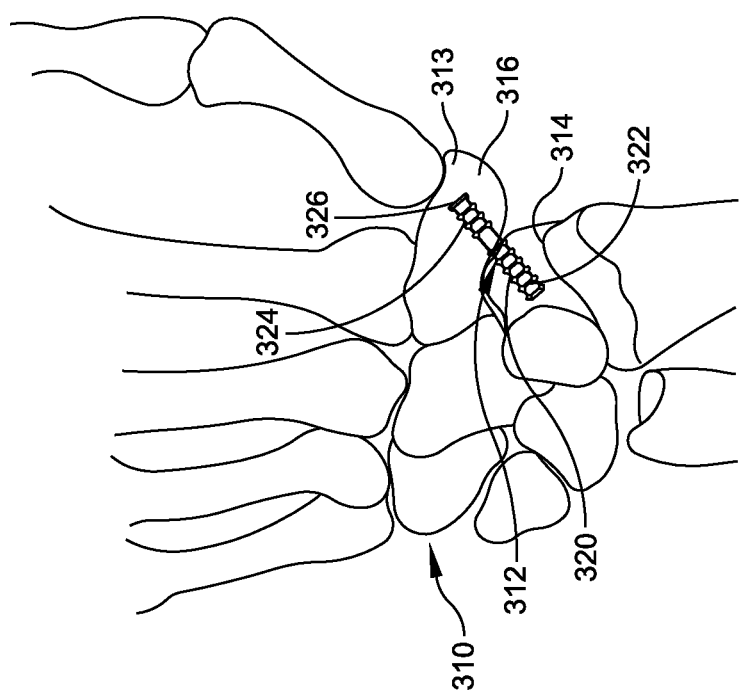
FIG. 3 is a top view of a portion of a hand and arm with a fusion implant having features of the present invention implanted therein.

FIG. 3 is simplified illustration of a portion of a body part 310 (e.g., a portion of a hand and an arm in this example) with an implant 312 that facilitates the fusion of a break in a bone 313, i.e. the scaphoid. Alternatively, the implant 312 can be utilized to facilitate the fusion of a break in another bone, such as the clavicle, humerus, ulna, radius, tibia, fibula, or some other bone.

As illustrated in FIG. 3, a portion of the bone 313 on either side of the break can be labeled as a first bone part 314 and a second bone part 316. In particular, the fracture in the bone 313 may be repaired by inserting the implant 312 at the fracture site and fixing the first bone part 314 and the second bone part 316 together with the use of the implant 312.

In this embodiment, prior to insertion of the implant 312 to facilitate the fusion of the broken bone 313, the proper amount of the first bone part 314 is removed and a first receiving aperture 320 is created in the first bone part 314 that is sized and shaped to receive a first portion 322 of the implant 312. Somewhat similarly, the proper amount of the second bone part 316 is removed and a second receiving aperture 324 is created in the second bone part 316 that is sized and shaped to receive a second portion 326 of the implant 312. For example, each receiving aperture 320, 324 can have a cross-section that is substantially circle-shaped, triangle-shaped, square-shaped, rectangle-shaped, pentagon-shaped, hexagon-shaped, octagon-shaped, or some other shape. With this design, the implant 312 is inserted and fitted within the receiving apertures 320, 324 of the bone parts 314, 316, respectively, and extends between the bone parts 314, 316.

Figure 4C:
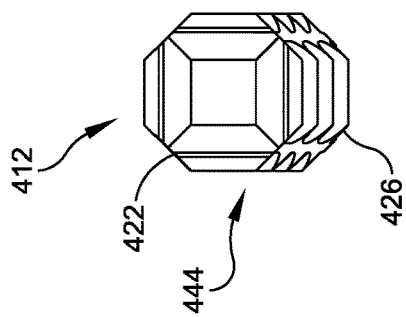
FIG. 4C is an end view of the fusion implant illustrated in FIG. 4A.
Figure 4A:
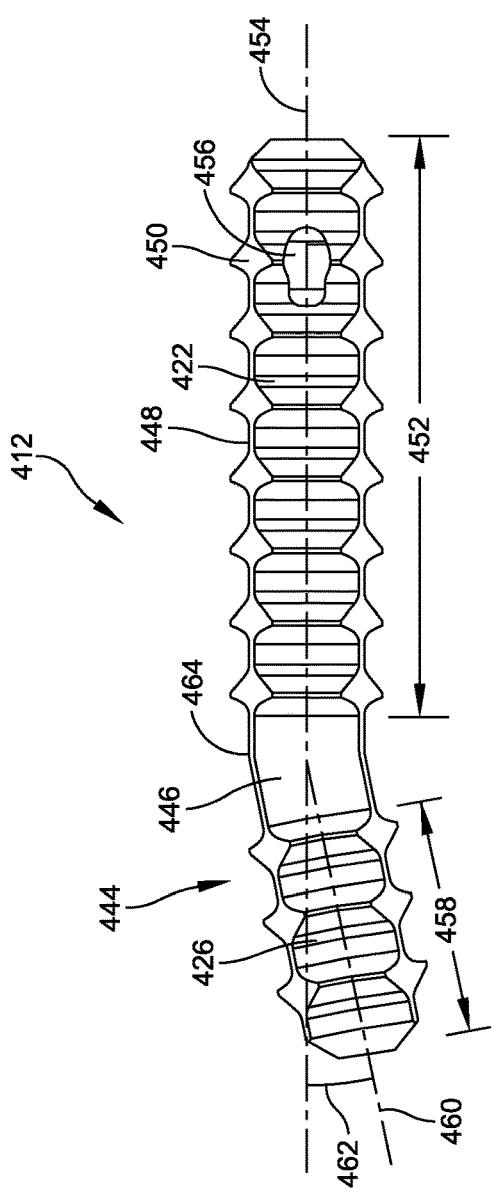
FIG. 4A is a side view of an embodiment of a fusion implant having features of the present invention.

FIG. 4A is a side view of an embodiment of a fusion implant 412 (an "implant") having features of the present invention. The design of the implant 412 can be varied. In the embodiment illustrated in FIG. 4A, the implant 412 includes an implant body 444 having a first (or proximal) portion 422, a second (or distal) portion 426, and an intermediate portion 446. Alternatively, the implant body 444 can be designed without the intermediate portion 446.

It should be noted that the use of the terms "first portion" and "second portion" is merely for ease of description, and is not intended to limit the scope or breadth of the present invention in any manner.

The first portion 422 is adapted to fit within a first receiving aperture, e.g., the first receiving aperture 20 illustrated in FIG. 1, that is created within a first bone part, e.g., the first bone part 14A illustrated in FIG. 1.

In this embodiment, the first portion 422 includes a plurality of substantially flat regions 448 and a plurality of ridges 450, such that the flat regions 448 and the ridges 450 alternate along a length 452 of the first portion 422. The ridges 450 are provided to inhibit the first portion 422 of the implant body 444 from being pulled out of the first receiving aperture of the first bone part. For example, in one embodiment, one or more of the ridges 450 can extend substantially transversely to a longitudinal axis 454 of the first portion 422 of the implant body 444. Alternatively, the first portion 422 can be designed without any ridges, and the entire length 452 of the first portion 422 can be substantially flat.

Additionally, in certain embodiments, the length 452 of the first portion 422 can be between approximately eight and fifteen millimeters. For example, in one specific embodiment, the length 452 of the first portion 422 can be approximately ten millimeters. In another specific embodiment, the length 452 of the first portion 422 can be approximately thirteen millimeters. Alternatively, the length 452 of the first portion 422 can be less than eight millimeters or greater than fifteen millimeters.

Further, as illustrated in FIG. 4A, the first portion 422 can include an orientation indicator 456 that indicates that the first portion 422 is designed to be inserted into the first bone part. For example, in one embodiment, the orientation indicator 456 can be an oval shaped, recessed area in the first portion 422 of the implant body 444. With this design, the first portion 422 of the implant body 444 will be properly inserted into the first bone part. More specifically, with this design, the physician inserting the implant body 444 will be able to quickly identify which end of the implant 412 is the first portion 422 that is to be inserted into the first (or proximal) bone part. Alternatively, the orientation indicator 456 can have a different design.

The second portion 426 is adapted to fit within a second receiving aperture, e.g., the second receiving aperture 24 illustrated in FIG. 1, that is created within a second bone part, e.g., the second bone part 16A illustrated in FIG. 1.

In this embodiment, similar to the first portion 422, the second portion 426 also includes a plurality of substantially flat regions 448 and a plurality of ridges 450, such that the flat regions 448 and the ridges 450 alternate along a length 458 of the second portion 426. In one embodiment, one or more of the ridges 450 can extend substantially transversely to a longitudinal axis 460 of the second portion 426 of the implant body 444. Alternatively, the second portion 426 can be designed without any ridges, and the entire length 458 of the second portion 425 can be substantially flat.

Additionally, in certain embodiments, the length 458 of the second portion 426 can be between approximately four and eight millimeters. For example, in one specific embodiment, the length 458 of the second portion 426 can be approximately six millimeters. Alternatively, the length 458 of the second portion 426 can be less than four millimeters or greater than eight millimeters.

Further, as illustrated in this embodiment, the second portion 426 can be angled relative to the first portion 422. Stated another way, the longitudinal axis 454 of the first portion 422 and the longitudinal axis 460 of the second portion 426 can define an orientation angle 462 therebetween. For example, in certain embodiments, the orientation angle 462 between the first portion 422 and the second portion 426 can be between approximately zero degrees and sixty degrees. In one specific embodiment, the orientation angle 462 between the first portion 422 and the second portion 426 can be approximately ten degrees. Alternatively, the orientation angle 462 between the first portion 422 and the second portion 426 can be greater than sixty degrees, or the second portion 426 can be substantially aligned with the first portion 422, i.e. the orientation angle 462 is zero degrees.

The intermediate portion 446 extends between the first portion 422 and the second portion 426. Moreover, the intermediate portion 446 is designed to extend substantially between the first bone part and the second bone part, e.g., be positioned at the joint (for example, the first joint 18A illustrated in FIG. 1) when the implant 412 is implanted in the body.

In certain embodiments, the intermediate portion 446 can comprise and/or include a depth indicator 464 that indicates when the first portion 422 of the implant body 444 is properly inserted into the first (or proximal) bone part and/or when the second portion 426 of the implant body 444 is properly inserted into the second (or distal) bone part. For example, the depth indicator 464 can include a joint line feature (e.g., half way between a gap in the teeth of the implant) to indicate an insertion depth of the first portion 422 into the first bone part and/or to indicate an insertion depth of the second portion 426 into the second bone part. Alternatively, the depth indicator 464 can be at the end of the ridges 450 on the first portion 422 of the implant body 444 and/or at the end of the ridges 450 on the second portion 426.

With this design, in certain embodiments, the first portion 422 of the implant body 444 is inserted by the physician until the depth indicator 464 is approximately flush with the end of the first bone part. This will ensure that the first portion 422 is properly inserted to the correct depth. This is particularly important for angled implants to ensure that the angled implant is properly positioned relative to the bone parts. Somewhat similarly, in certain embodiments, the second portion 426 of the implant body 444 is inserted by the physician until the depth indicator 464 is approximately flush with the end of the second bone part. This will ensure that the second portion 426 is properly inserted to the correct depth.

In some embodiments, one or more of the first portion 422, the second portion 426 and the intermediate portion 446 of the implant body 444 can be made of bone. For example, in certain embodiments, each portion 422, 426, 446 of the implant body 444 can be made of cortical bone. Moreover, each portion 422, 426, 446 can be made of bone that is partially demineralized. In one embodiment, one or more of the portions 422, 426, 446 can be a partially demineralized human cortical bone allograft.

In certain embodiments, because cortical bone is anisotropic, the cortical bone's longitudinal axis would be aligned with the longitudinal axes 454, 460 of the implant body 444. In some cases it may be optimal to orient the cortical bone in the opposite direction (90°) to take advantage of the mechanical properties of the bone.

Other sources of the bone material may be used and include, but is not limited to, bovine.

As provided herein, the implant 412 can have the high strength of cortical bone to support the fusion. It can further have the osteoconductive properties of allograft bone but the surface demineralization will give it osteoinductive properties to help with the fusion process. The demineralization will also make the outside soft so that the implant 412 can be placed into the prepared bone to be treated. The demineralized layer extends from the surface of the bone toward the center of the implant body 444. The demineralized portion may extend from the surface to the core depending on the application. In an alternative embodiment, there will not be any demineralization of the outer surface of the implant body 444. This will result in a naturally hard implant 412.

Figure 4B:
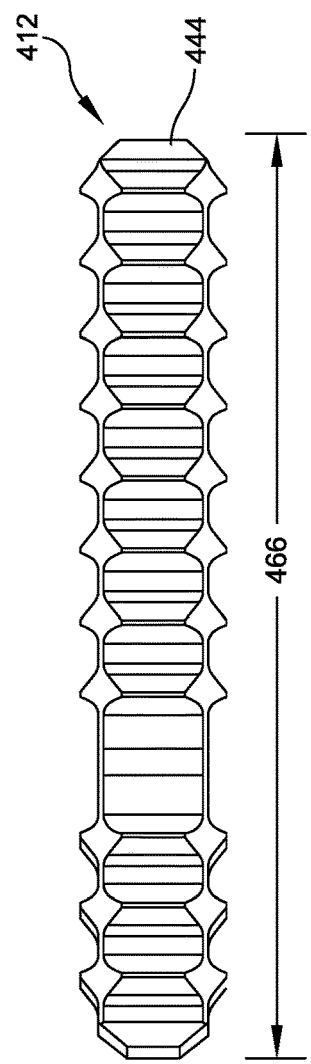
FIG. 4B is a bottom view of the fusion implant illustrated in FIG. 4A.

FIG. 4B is a bottom view of the implant 412 illustrated in FIG. 4A. In particular, FIG. 4B illustrates that the implant body 444 has an overall length 466, which can be between approximately twelve and twenty-three millimeters. For example, in one specific embodiment, the overall length 466 of the implant body 444 can be approximately sixteen millimeters. In another specific embodiment, the overall length 466 of the implant body 444 can be approximately nineteen millimeters. Alternatively, the overall length 466 of the implant body 466 can be less than twelve millimeters or greater than twenty-three millimeters.

FIG. 4C is an end view of the implant 412 illustrated in FIG. 4A. As illustrated in FIG. 4C, the implant body 444, i.e. one or more of the first portion 422, the second portion 426 and the intermediate portion 446 (illustrated in FIG. 4A), can have a cross-section that is substantially octagon-shaped. Alternatively, the implant body 444 can have a cross-section that is substantially triangle-shaped, square-shaped, rectangle-shaped, pentagon-shaped, hexagon-shaped, or some other shape which may be regular or irregular. It should be noted that references to the cross-sectional shapes of the implant bodies herein refer to the cross-sectional shapes at the ridges, i.e., ridges 450 in the case of implant body 444 and corresponding ridges in other implant bodies described herein. The only exception to this is when the first portion of the implant body is threaded. As noted above, with this design, the non-circular cross-sectional shape of the implant body 444 functions to inhibit relative movement between the first portion 422 of the implant body 444 and the first receiving aperture of the first bone part, and the second portion 426 of the implant body 444 and the second receiving aperture of the second bone part.

Figure 5B:
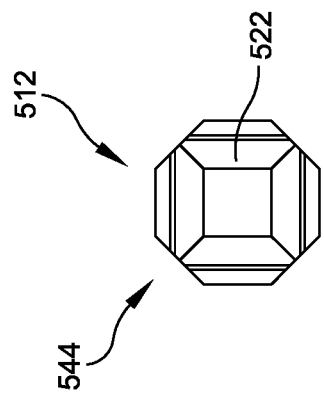
FIG. 5B is an end view of the fusion implant illustrated in FIG. 5A.
Figure 5A:
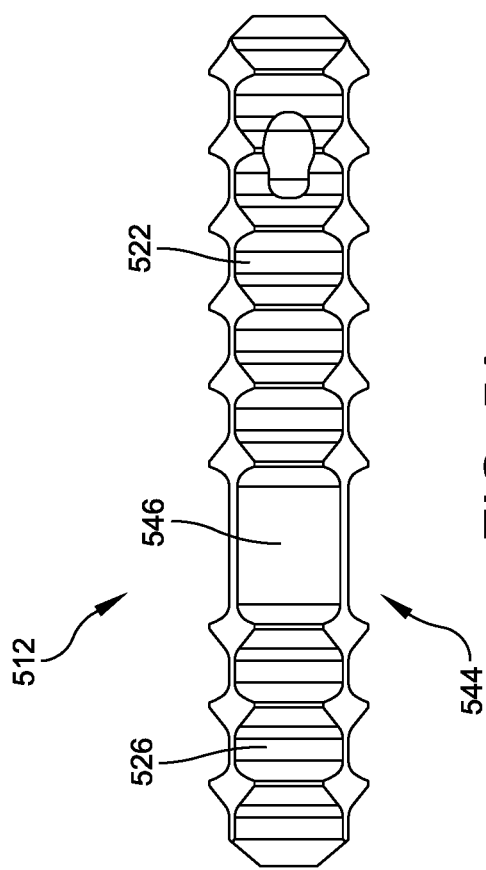
FIG. 5A is a side view of another embodiment of a fusion implant having features of the present invention.

FIG. 5A is a side view of another embodiment of a fusion implant 512 (an "implant") having features of the present invention. The implant 512 is substantially similar to the implant 412 illustrated and described above in relation to FIGS. 4A-4C. For example, the implant 512 includes an implant body 544 having a first portion 522, a second portion 526, and an intermediate portion 546 that are substantially similar to the first portion 422, the second portion 426, and the intermediate portion 446 illustrated and described above in relation to FIGS. 4A-4C. However, in the embodiment illustrated in FIG. 5A, the first portion 522 and the second portion 526 of the implant body 544 are substantially aligned. Stated another way, in this embodiment, the implant body 544 is generally straight beam shaped, with no orientation angle (i.e. an orientation angle of zero degrees) between the first portion 522 and the second portion 526.

FIG. 5B is an end view of the implant 512 illustrated in FIG. 5A. Similar to the previous embodiment, as illustrated in FIG. 5B, the implant body 544, i.e. one or more of the first portion 522, the second portion 526 (illustrated in FIG. 5A) and the intermediate portion 546 (illustrated in FIG. 5A), can have a cross-section that is substantially octagon-shaped. Alternatively, the implant body 544 can have a cross-section that is substantially triangle-shaped, square-shaped, rectangle-shaped, pentagon-shaped, hexagon-shaped, or some other shape. With this design, the non-circular cross-sectional shape of the implant body 544 again functions to inhibit relative movement between the first portion 522 of the implant body 544 and the first receiving aperture of the first bone part, and the second portion 526 of the implant body 544 and the second receiving aperture of the second bone part.

FIG. 6A is a side view of still another embodiment of a fusion implant 612 (an "implant") having features of the present invention. The implant 612 is somewhat similar to the implants 412, 512 illustrated and described above. For example, the implant 612 includes an implant body 644 having a first portion 622, a second portion 626, and an intermediate portion 646 that are somewhat similar to the first portions 422, 522, the second portions 426, 526, and the intermediate portions 446, 546 illustrated and described above.

As illustrated in FIG. 6A, similar to the embodiment illustrated in FIGS. 4A-4C, the second portion 626 is again angled relative to the first portion 622. Stated another way, a longitudinal axis 654 of the first portion 622 and a longitudinal axis 660 of the second portion 626 can define an orientation angle 662 therebetween. For example, in certain embodiments, the orientation angle 662 between the first portion 622 and the second portion 626 can be between approximately zero degrees and sixty degrees. In one specific embodiment, the orientation angle 662 between the first portion 622 and the second portion 626 can be approximately ten degrees. Alternatively, the orientation angle 662 between the first portion 622 and the second portion 626 can be greater than sixty degrees, or the second portion 626 can be substantially aligned with the first portion 622, i.e. the orientation angle 662 is zero degrees.

FIG. 6B is an end view of the implant 612 illustrated in FIG. 6A. In particular, FIG. 6B illustrates that the implant body 644, i.e. one or more of the first portion 622, the second portion 626 and the intermediate portion 646 (illustrated in FIG. 6A), has a cross-section that is substantially rectangle-shaped. Alternatively, the implant body 644 can have a cross-section that is substantially triangle-shaped, square-shaped, pentagon-shaped, hexagon-shaped, octagon-shaped, or some other shape. With this design, the non-circular cross-sectional shape of the implant body 644 again functions to inhibit relative movement between the first portion 622 of the implant body 644 and the first receiving aperture of the first bone part, and the second portion 626 of the implant body 644 and the second receiving aperture of the second bone part.

Figure 7A:
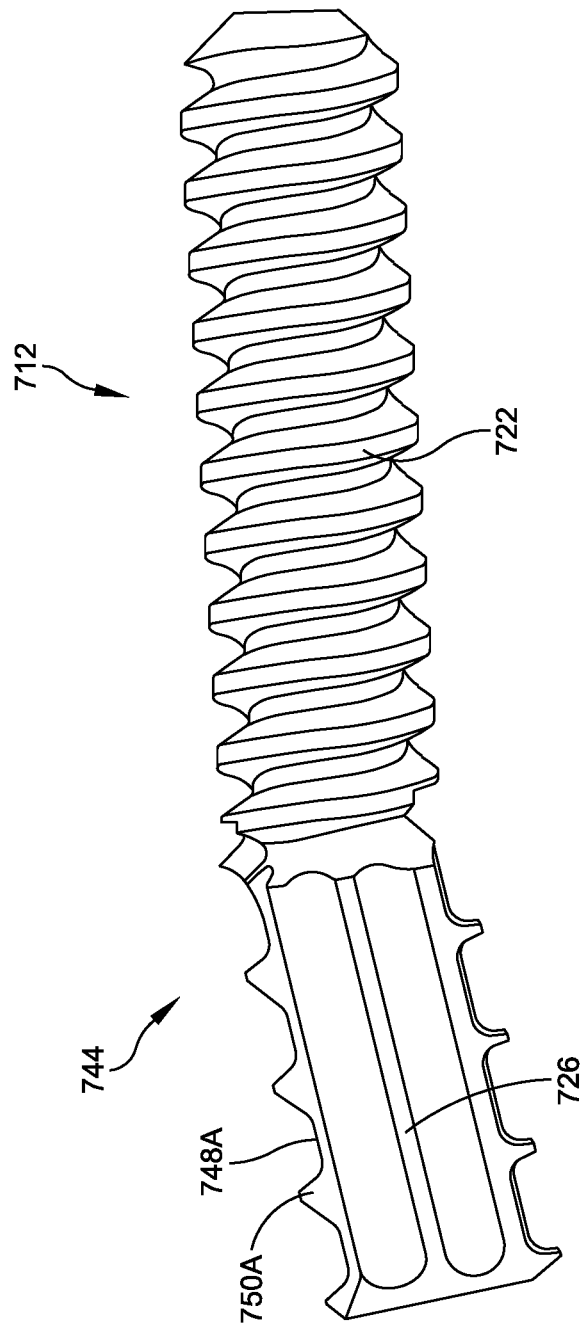
FIG. 7A is a side view of yet another embodiment of a fusion implant having features of the present invention.

FIG. 7A is a side view of yet another embodiment of a fusion implant 712 (an "implant") having features of the present invention. The implant 712 is somewhat similar to the implants 412, 512, 612 illustrated and described above. For example, the implant 712 includes an implant body 744 having a first portion 722 and a second portion 726 that are somewhat similar to the first portions 422, 522, 622 and the second portions 426, 526, 626 illustrated and described above. Additionally, as illustrated in FIG. 7A, similar to the embodiments illustrated in FIGS. 4A-4C and 6A-6B, the second portion 726 is again angled relative to the first portion 722.

However, in the embodiment illustrated in FIG. 7A, the first portion 722 is threaded and includes a substantially circular cross-section to enable the first portion 722 to be threaded into a first receiving aperture, e.g., the first receiving aperture 20 illustrated in FIG. 1, that is created within a first bone part, e.g., the first bone part 14A illustrated in FIG. 1.

Figure 7B:
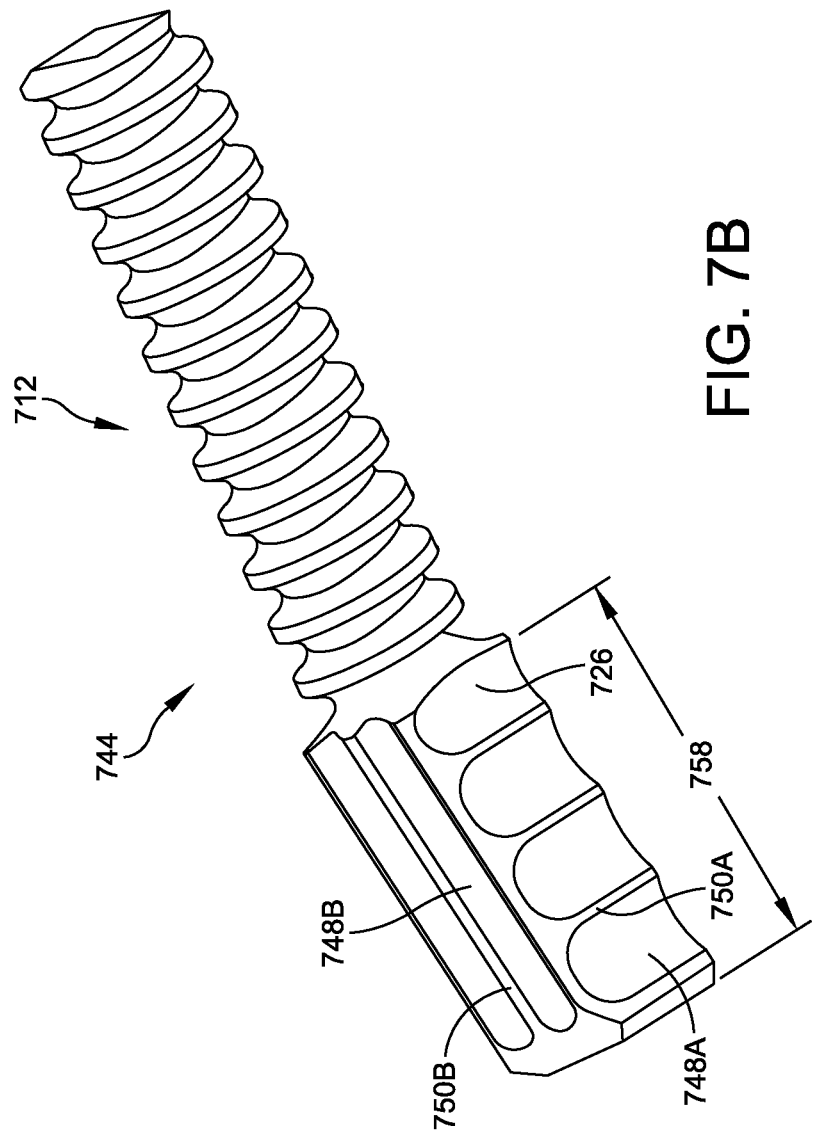
FIG. 7B is a perspective view of the fusion implant illustrated in FIG. 7A.

FIG. 7B is a perspective view of the implant 712 illustrated in FIG. 7A. In particular, FIG. 7B illustrates that the second portion 726 of the implant body 744 has a cross-section that is substantially square-shaped or rectangle-shaped. Alternatively, the second portion 726 can have a cross-section that is substantially triangle-shaped, pentagon-shaped, hexagon-shaped, octagon-shaped, or some other shape. With this design, the non-circular cross-sectional shape of the second portion 726 functions to inhibit relative movement between the second portion 726 of the implant body 744 and the second receiving aperture of the second bone part. Still alternatively, the second portion 726 can be threaded and/or can include e substantially circular cross-section to enable the second portion 726 to be threaded into a second receiving aperture, e.g., the second receiving aperture 24 illustrated in FIG. 1, that is created within a second bone part, e.g., the second bone part 16A illustrated in FIG. 1.

Additionally, FIG. 7B illustrates that the second portion 726 of the implant body 744 includes a plurality of first flat regions 748A and a plurality of first ridges 750A, such that the first flat regions 748A and the first ridges 750A alternate along a length 758 of the second portion 726. Further, as more clearly illustrated in FIG. 7A, the plurality of first flat regions 748A and the plurality of first ridges 750A can be positioned on each of two opposite sides of the second portion 726 of the implant body 744. Alternatively, the second portion 726 can include alternating first flat regions 748A and first ridges 750A on more than two sides or less than two sides of the second portion 726.

Moreover, FIG. 7B illustrates that the second portion 726 includes a plurality of second flat regions 748B and a plurality of second ridges 750B that alternate such that each of the plurality of second flat regions 748B and the plurality of second ridges 750B extend in a direction substantially parallel to the length 758 of the second portion 726. In one embodiment, the plurality of second flat regions 748B and the plurality of second ridges 750B can be positioned on each of two opposite sides of the second portion 726 of the implant body 744. Alternatively, the second portion 726 can include alternating second flat regions 748B and second ridges 750B on more than two sides or less than two sides of the second portion 726.

FIGS. 8-10 illustrate embodiments wherein implant bodies having non-circular cross-sectional shapes are implanted in receiving apertures having circular cross-sectional shapes. The illustrated cross-sectional shapes are perpendicular to the longitudinal central axes of the implant bodies and the receiving apertures. In the preferred embodiments, the implant bodies having non-circular cross-sectional shapes are press-fit into the circular receiving apertures, the central axes of the implant bodies and receiving apertures being substantially coaxial. Adhesives are not required to prevent the implant bodies from rotating within the aperture walls because the implant bodies are sized relative to the size of the aperture opening to allow insertion of the bodies into the opening under pressure. As a result, ridges of the implant bodies are pressed against the inside walls of the receiving apertures and the inserted implant bodies are prevented from rotating. The term "circular aperture" as used herein means a receiving aperture having a circular shaped cross-section when the section is taken perpendicular to the central axis of the aperture.

Figure 8A:
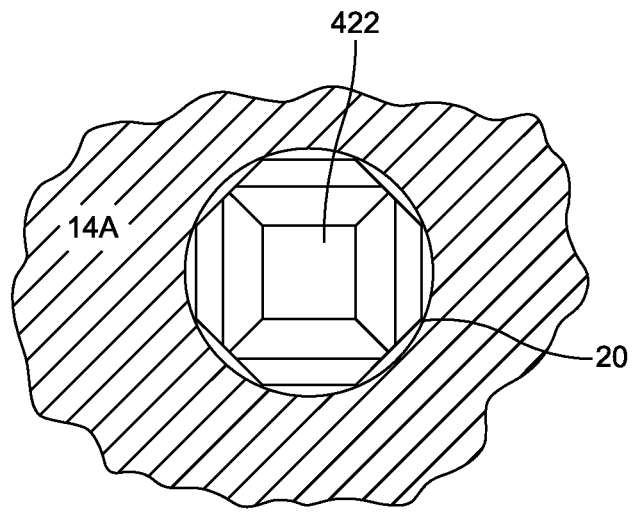
FIG. 8A is a partial section view illustrating a bone part in section having a circular receiving aperture and an end view of a first portion of an implant having an octagonal cross-section.
Figure 8B:
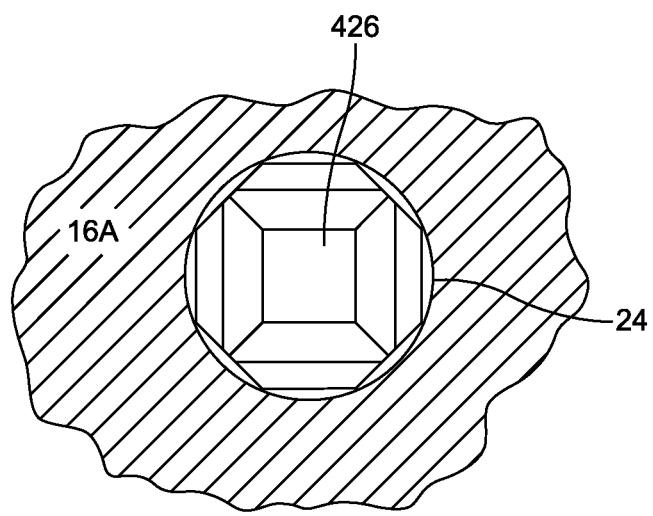
FIG. 8B is a partial section view illustrating a bone part in section having a circular receiving aperture and an end view of a second portion of an implant having an octagonal cross-section.

Fusion implant 412, having a substantially octagon shaped cross-section, is illustrated in FIG. 4A and is shown in FIGS. 8A and 8B after it has been implanted in bone parts 14A and 16A, respectfully. First portion 422 is press-fit into circular receiving aperture 20 and second portion 426 is press-fit into receiving aperture 24. Implants having octagonal cross-sections are a preferred embodiment of the invention.

Figure 9A:
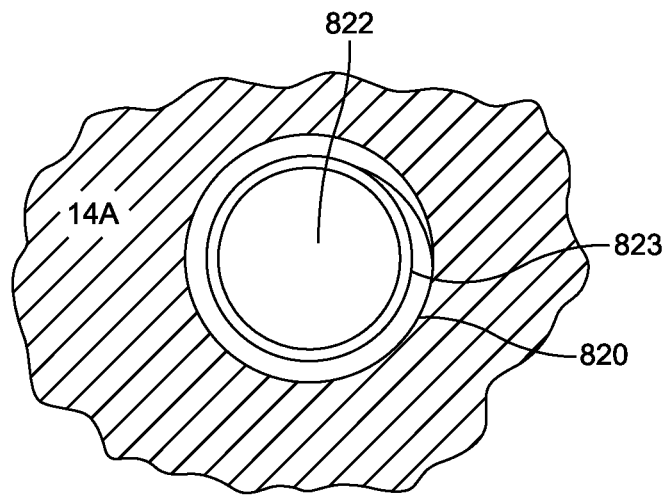
FIG. 9A is a partial section view illustrating a bone part in section having a circular receiving aperture and an end view of a first portion of an implant having external threads.
Figure 9B:
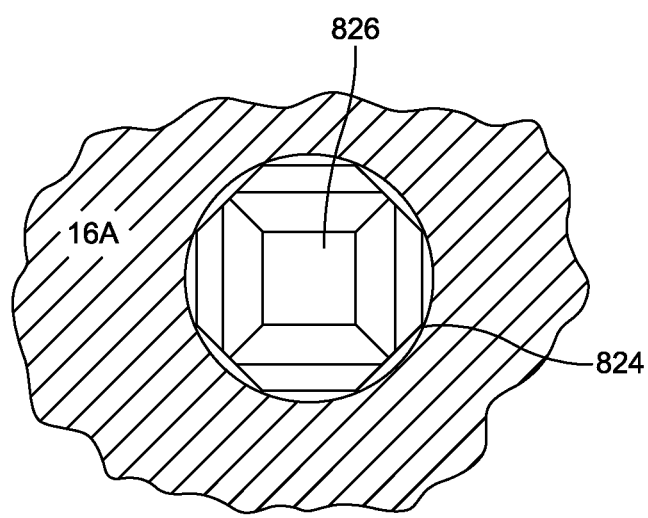
FIG. 9B is a partial section view illustrating a bone part in section having a circular receiving aperture and an end view of a second portion of an implant having an octagonal cross-section.

In FIGS. 9A and 9B a fusion implant similar to fusion implant 712 illustrated in FIGS. 7A and 7B, is shown in bone portions 14A and 16A, respectively. First portion 822, provided with threads 823, is screwed into aperture 820 of bone part 14A. The threads 823 may be self-tapping or aperture 820 can be threaded. Then the second portion 826, having an octagonal cross-section, is press-fit into circular aperture 824 of bone part 16A. This is also a preferred embodiment because the second portion 826 has an octagonal cross-section.

Other non-circular cross-sectional shapes can be used for the fusion implants of the invention as has been stated throughout the present specification. The fusion implants can have first and second portions with the same or different cross-sectional shapes. For example, the first portion can be threaded or triangular, square, rectangular, pentagonal, hexagonal or octagonal in cross-section and the second portion can be triangular, square, rectangular, pentagonal, hexagonal, or octagonal in cross-section.

Figure 10A:
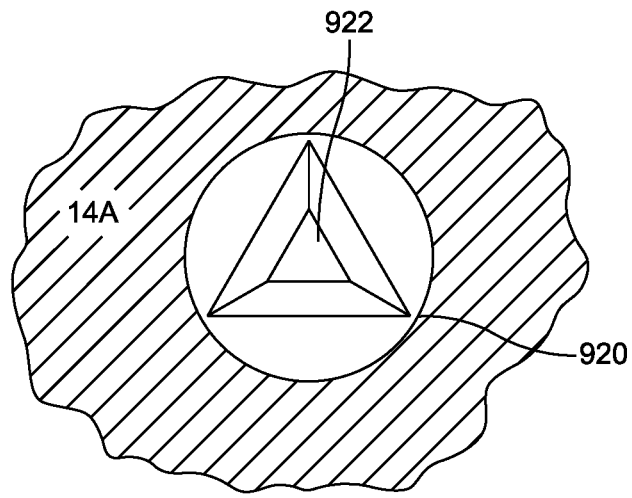
FIG. 10A is a partial section view illustrating a bone part in section having a circular receiving aperture and an end view of a first portion of an implant having a triangular cross-section.

FIG. 10A illustrates an implant first portion 922 having a triangular cross-section which has been press-fit into a circular aperture 920 of bone part 14A.

Figure 10B:
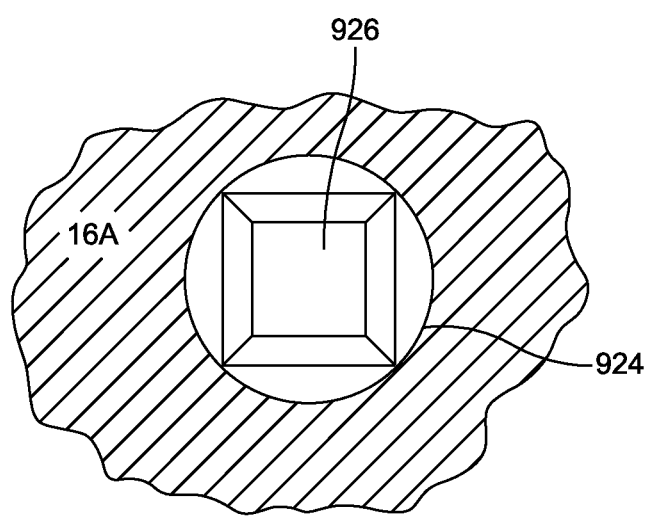
FIG. 10B is a partial section view illustrating a bone part in section having a circular receiving aperture and an end view of a second portion of an implant having a square or rectangular cross-section.

FIG. 10B illustrates an implant second portion 926 having a square or rectangular cross-section which has been press-fit into a circular aperture 924 of bone part 16A.

Figure 11A:
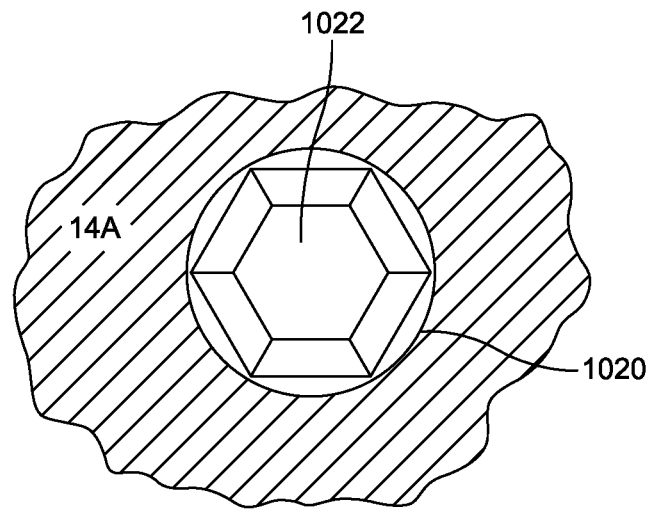
FIG. 11A is a partial section view illustrating a bone part in section having a circular receiving aperture and an end view of a first portion of an implant having a hexagonal cross-section.

FIG. 11A illustrates an implant first portion 1022 having a hexagonal cross-section which has been press-fit into a circular aperture 1020 of bone part 14A.

Figure 11B:
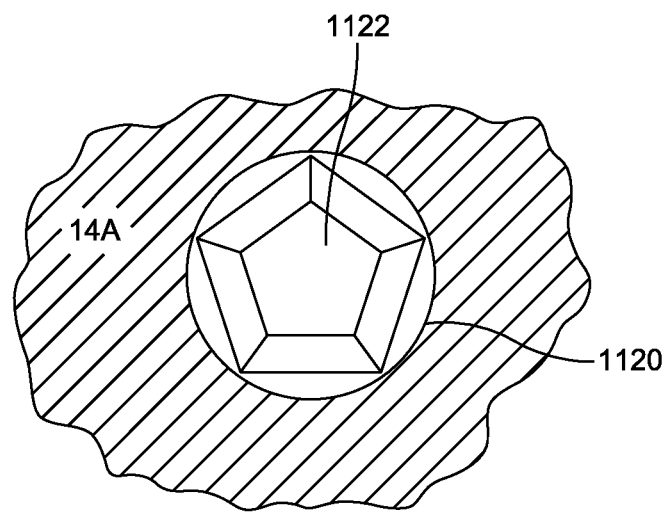
FIG. 11B is a partial section view illustrating a bone part in section having a circular receiving aperture and an end view of a first portion of an implant having a pentagonal cross-section.

FIG. 11B illustrates an implant first portion 1122 having a pentagonal cross-section which has been press-fit into circular aperture 1120 of bone part 14A.

Figure 12A:
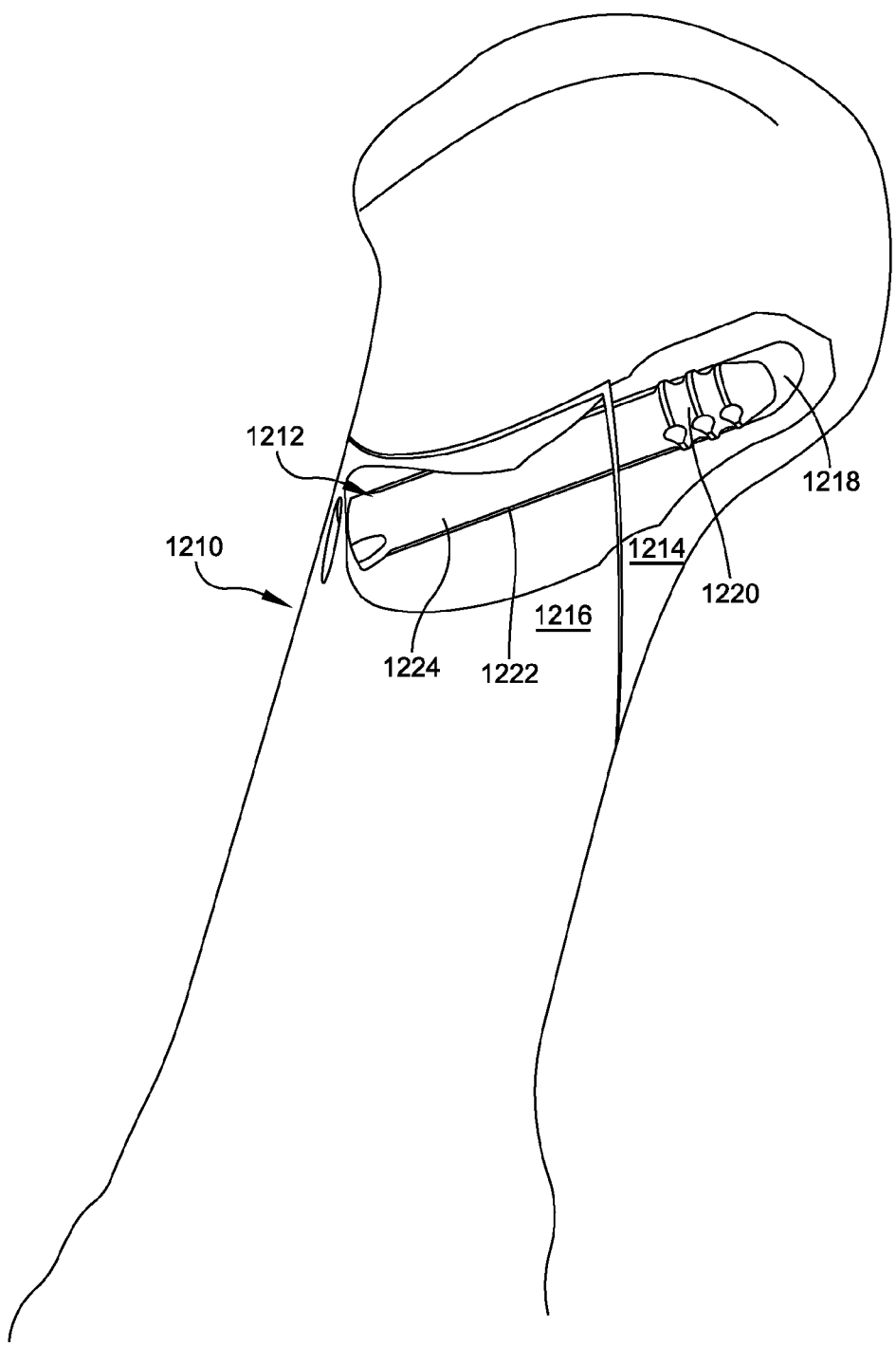
FIGS. 12A-12C illustrate a Chevron osteotomy of the first metatarsal bone with three alternative fusion implants having features of the present invention implanted therein.
Figure 12B:
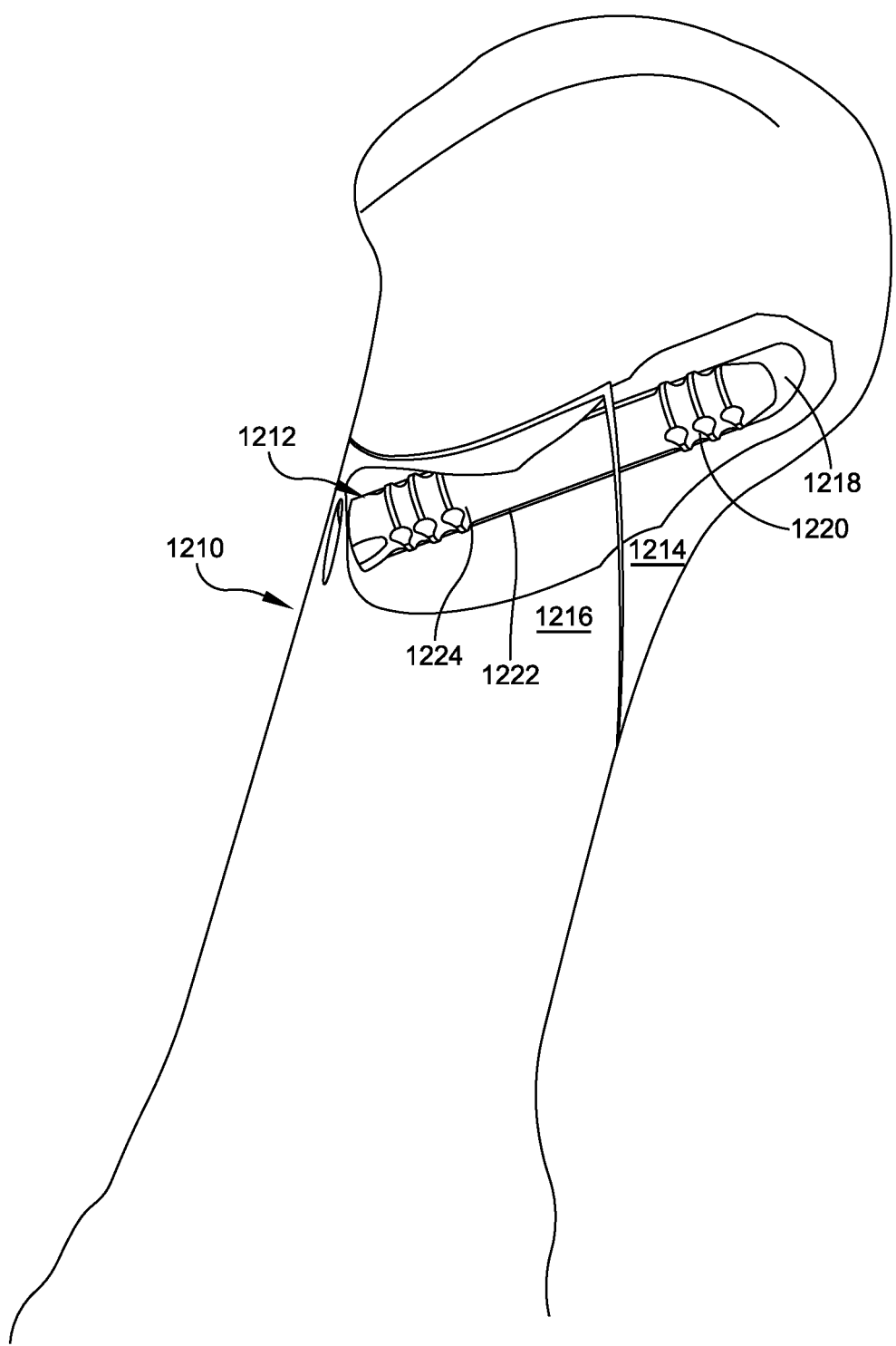
Figure 12C:
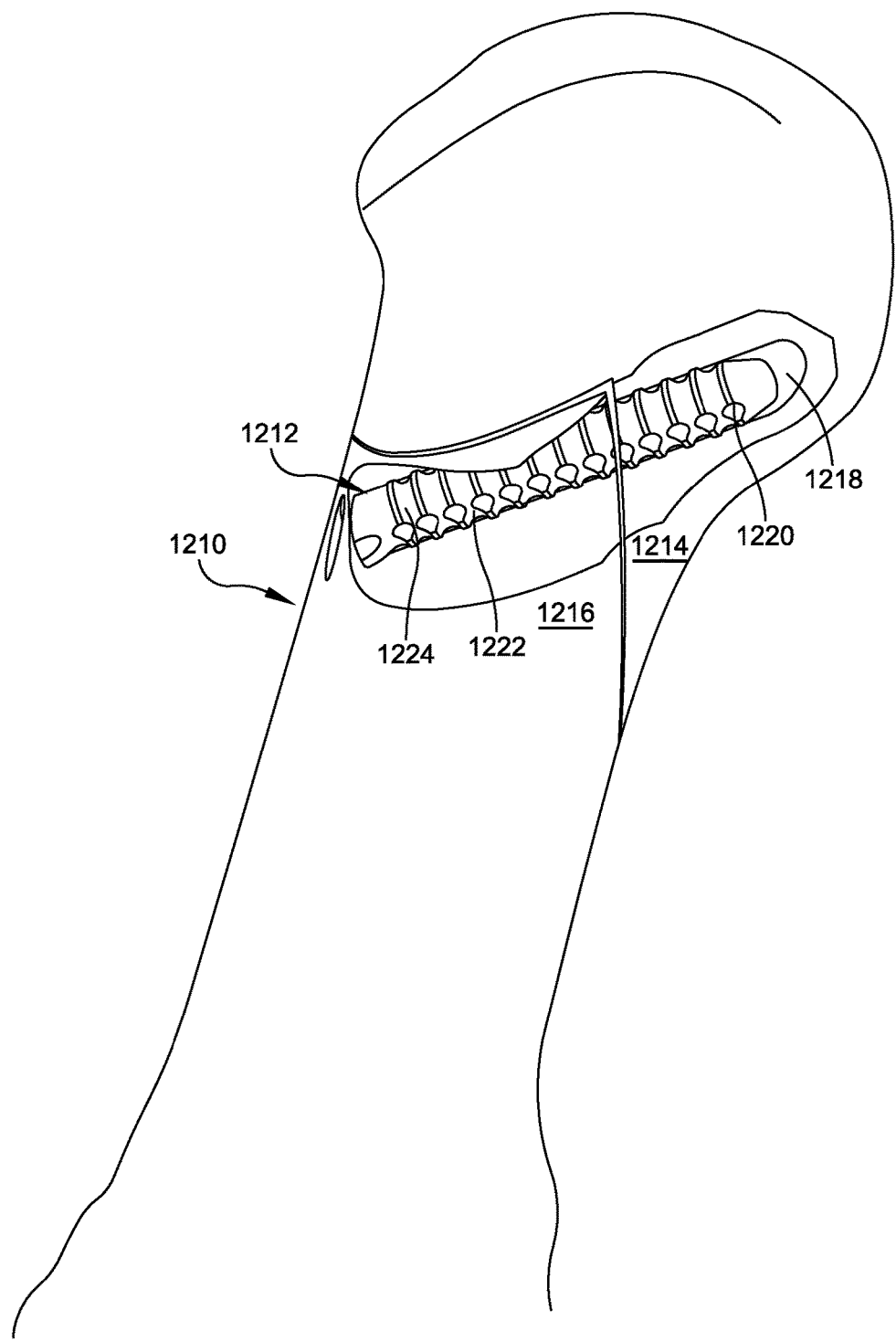

FIGS. 12A-12C illustrate a Chevron osteotomy of the first metatarsal bone with three alternative fusion implants having features of the present invention implanted therein. FIGS. 12A-12C illustrate a body part 1210, e.g., a first metatarsal bone in this example, with a fusion implant 1212 having features of the present invention implanted therein. More particularly, FIGS. 12A-12C illustrate three alternative fusion implants 1212 that facilitate the fusion of a first bone part 1214 and a second bone part 1216 within the body part 1210. It should be noted that in FIGS. 12A-12C, the bone is cut-away to expose the implant 1212. However, the bone is not cut-away at the joint of the bone parts 1214, 1216. Thus, the implant 1212 looks cut in FIGS. 12A-12C, however, the implant 1212 is continuous in these Figures.

In this embodiment, prior to the insertion of the fusion implant 1212, during an osteotomy procedure, a portion of a bone is cut so as to define the first bone part 1214 and the second bone part 1216. Subsequently, the bone parts 1214, 1216 are aligned as desired and the bone parts 1214, 1216 are then prepared by reaming a hole that is adapted to receive the fusion implant 1212. In particular, during this process, a first (or leading) receiving aperture 1218 is created in the first bone part 1214 that is sized and shaped to receive a first (or leading) portion 1220 of the fusion implant 1212, and a second (or trailing) receiving aperture 1222 is created in the second bone part 1216 that is sized and shaped to receive a second (or trailing) portion 1224 of the fusion implant 1212. In certain embodiments, each receiving aperture 1218, 2122 can have a cross-section that is substantially circle-shaped that is adapted to receive the fusion implant 1212, which can also have a cross-section that is substantially circle-shaped. In one such embodiment, the first receiving aperture 1218 can have a diameter that is slightly smaller than a diameter of the first portion 1220 of the fusion implant 1212 and/or the second receiving aperture 1222 can have a diameter that is slightly smaller than a diameter of the second portion 1224 of the fusion implant 12. With this design, a snug fit can be achieved between the fusion implant 1212 and the corresponding bone parts 1214, 1216. Alternatively, each receiving aperture 1218, 1222 can have a cross-section that is a different size and/or a different shape than described above as long as the second receiving aperture is large enough to allow the first portion of the fusion implant to pass through the second receiving aperture on the way to the first receiving aperture. In certain alternative embodiments, each receiving aperture 1218, 1222 can have a cross-section that is substantially triangle-shaped, square-shaped, rectangle-shaped, pentagon-shaped, hexagon-shaped, octagon-shaped, or some other shape.

It should be noted that the use of the terms "first bone part" and "second bone part", "first receiving aperture" and "second receiving aperture" is merely for ease of description, and is not intended to limit the scope or breadth of the present invention in any manner.

After the bone parts 1214, 1216 have been prepared, the fusion implant 1212 can be placed into the bone, i.e. into the bone parts 1214, 1216, by either axially driving or turning through a female drive feature on the back or distal end of the fusion implant 1212. An example of a female drive feature would be a hexagonal recess, a square recess, a slotted recess for a conventional or Phillips head screwdriver or the like. Additionally, the fusion implant 1212 is placed through the two bone parts 1214, 1216 in one direction, entering initially through the second bone part 1216 and then advancing fully through to the first bone part 1214. At this point, the first portion 1220 of the fusion implant 1212 will be effectively positioned within the first receiving aperture 1218 in the first bone part 1214, and the second portion 1224 of the fusion implant 1212 will be effectively positioned within the second receiving aperture 1222 in the second bone part 1216. Moreover, the fusion implant 1212, thus implanted, will effectively draw the bone parts 1214, 1216 together.

Figure 13A:
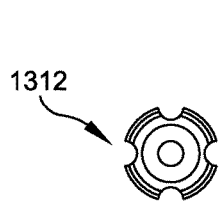
FIGS. 13A-13C are alternative views of an embodiment of a fusion implant having features of the present invention.
Figure 13C:
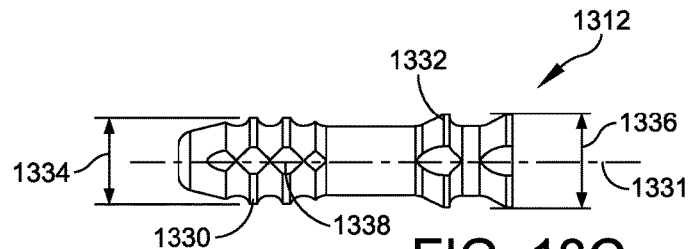
Figure 13B:
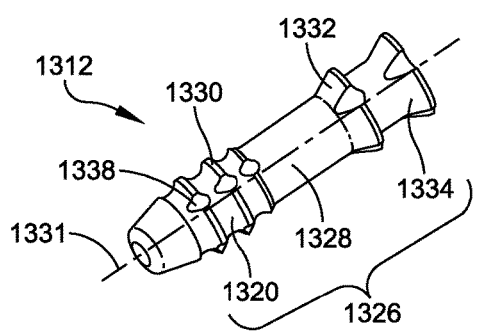

FIGS. 13A-13C are alternative views of an embodiment of a fusion implant 1312 having features of the present invention. The design of the fusion implant 1312 can be varied. In the embodiment illustrated in FIGS. 13A-13C, the fusion implant 1312 includes an implant body 1326 having a first (or leading) portion 1320, a second (or trailing) portion 1324, and an intermediate portion 1328 that is coextensive with and extends between the first portion 1320 and the second portion 1324. Alternatively, the implant body 1326 can be designed without the intermediate portion 1328, and the first portion 1320 can be directly coextensive with the portion 1324.

The first portion 1320 is adapted to fit within a first receiving aperture, e.g., the first receiving aperture 1218 illustrated in FIGS. 12A-12C, that is created within a first bone part, e.g., the first bone part 1214 illustrated in FIGS. 12A-12C. Somewhat similarly, the second portion 1324 is adapted to fit within a second receiving aperture, e.g., the second receiving aperture 1222 illustrated in FIGS. 12A-12C, that is created within a second bone part, e.g., the second bone part 1216 illustrated in FIGS. 12A-12C.

In the embodiment illustrated in FIGS. 13A-13C, the first portion 1320 includes a plurality of spaced apart first ridges 1330 or teeth that extend circumferentially substantially completely about the implant body 1326. Stated another way, in this embodiment, the first ridges 1330 extend substantially transversely to a longitudinal axis 1331 of the implant body 1326. The number of first ridges 1330 and/or the specific design or orientation of the first ridges 1330 can be varied to suit the particular design requirements of the fusion implant 1312. Somewhat similarly, in this embodiment, the second portion 1324 includes a plurality of spaced apart second ridges 1332 or teeth that extend circumferentially substantially completely about the implant body 1326. Stated another way, the second ridges 1332 extend substantially transversely to the longitudinal axis 1331 of the implant body 1326. The number of second ridges 1332 and/or the specific design or orientation of the second ridges 1332 can be varied to suit the particular design requirements of the fusion implant 1312. Moreover, in certain embodiments, the spacing between the first ridges 1330 is different than the spacing between the second ridges 1332. With this design, the fusion implant 1312 is better able to effectively draw the bone parts 1214, 1216 together so as to better enable or enhance the healing process after the osteotomy procedure.

Additionally, in one embodiment, as illustrated, the first portion 1320 has a first (or leading) diameter 1334, and the second portion 1324 has a second (or trailing) diameter 1336 that is greater than or equal to the first diameter 1334. This enables the first portion 1320 to be easily inserted through the second receiving aperture 1222 prior to being inserted and fitted snugly into the first receiving aperture 1218.

Further, in the embodiment illustrated in 13A-13C, the first portion 1320 and the second portion 1324 each include a plurality of spaced apart longitudinal grooves 1338 or flutes that extend substantially perpendicularly to the ridges 1330, 1332 in the first portion 1320 and the second portion 1324, respectively. Moreover, the grooves 1338 extend substantially parallel to the longitudinal axis 1331 of the implant body 1326. The grooves 1338 are provided to assist in the insertion of the fusion implant 1312 within the bone parts 1214, 1216, and/or to inhibit relative rotation between the first bone part 1214 and the second bone part 1216 after insertion of the fusion implant 1312. Alternatively, one or both of the first portion 1320 and the second portion 1324 can be designed without the longitudinal grooves 1338.

In this embodiment, as noted above, the intermediate portion 1328 is coextensive with and extends between the first portion 1320 and the second portion 1324. As illustrated, the intermediate portion 1328 is substantially cylindrical shaped. Additionally, in this embodiment, the intermediate portion 1328 is devoid of any surface features, such as the ridges 1330, 1332 or teeth included with the first portion 1320 and the second portion 1324, respectively. Stated another way, the intermediate portion 1328 can be described as a lag portion in the middle with an absence of press-fit material.

In some embodiments, one or more of the first portion 1320, the second portion 1324 and the intermediate portion 1328 of the implant body 1328 can be made of bone. For example, in certain embodiments, each portion 1320, 1324, 1328 of the implant body 1326 can be made of human or animal cortical bone. Moreover, each portion 1320, 1324, 1328 can be made of bone that is partially demineralized or non-demineralized. In one embodiment, one or more of the sections 1320, 1324, 1328 can be a partially demineralized human cortical bone allograft.

In certain embodiments, because cortical bone is anisotropic, the cortical bone's longitudinal axis would be aligned with the longitudinal axis 1331 of the implant body 1326. In some cases it may be optimal to orient the cortical bone in the opposite direction (90°) to take advantage of the mechanical properties of the bone. Other sources of the bone material may be used and include, but is not limited to, bovine.

As provided herein, the fusion implant 1312 can have the high strength of cortical bone to support the fusion. It can further have the osteoconductive properties of allograft bone but the surface demineralization will give it osteoinductive properties to help with the fusion process. The demineralization will also make the outside soft so that the fusion implant 1312 can be implanted into the bone parts 1214, 1216 to be fused. The demineralized layer extends from the surface of the bone toward the center of the implant body 1326. The demineralized portion may extend from the surface to the core depending on the application. In an alternative embodiment, there will not be any demineralization of the outer surface of the implant body 1326, i.e. the implant body 1326 is non-demineralized. This will result in a naturally hard implant 1312.

Figure 13D:
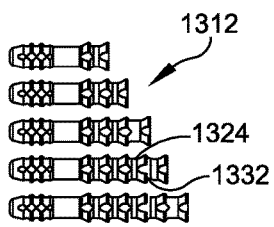
FIG. 13D is a side view of different sizes of the fusion implant illustrated in FIGS. 13A-13C.

FIG. 13D is a side view of alternative sizes and/or lengths of the fusion implant 1312 illustrated in FIGS. 12A-12C. In particular, FIG. 13D illustrates the fusion implant 1312 wherein the second portion 1324 includes differing numbers of second ridges 1332 depending upon the size and/or length of the fusion implant 1312. The alternative sizes and/or lengths of the fusion implant 1312 can be chosen based on the size of the bone parts 1214, 1216 (illustrated in FIGS. 12A-12C) that are being fused or drawn together with the fusion implant 1312.

Figure 13E:
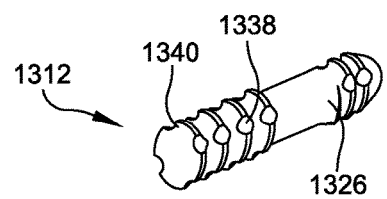
FIG. 13E is a perspective view of one of the sizes of the fusion implant illustrated in FIG. 13D.

FIG. 13E is a perspective view of one of the sizes of the fusion implant 1312 illustrated in FIG. 13D. In particular, FIG. 13E is a perspective view of one of the intermediate sizes, i.e. size 14, of the fusion implant 1312 illustrated in FIG. 213D.

As shown in FIG. 13E, the longitudinal grooves 1338 within the second portion 1324 extend fully to an end 1340 of the implant body 1326. With this design, the fusion implant 1212 can be driven into the bone parts 1214, 1216 (illustrated in FIGS. 12A-12C) with a driving tool (not illustrated) having tabs that engage with the grooves 1338 at or substantially near the end 1340 of the second portion 1324 of the implant body 1326. Alternatively, the fusion implant 1312 can be driven into the bone parts 1214, 1216 in a different manner and/or with a different driving tool.

Figure 14:
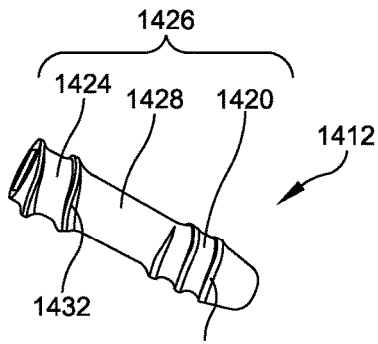
FIG. 14 is a perspective view of another embodiment of a fusion implant having features of the present invention.

FIG. 14 is a perspective view of another embodiment of a fusion implant 1412 having features of the present invention. As illustrated, the fusion implant 1412 is somewhat similar to the fusion implant 1312 illustrated and described above in relation to FIGS. 12A-12C. In particular, in this embodiment, the fusion implant 1412 includes an implant body 1426 having a first (or leading) portion 1420, a second (or trailing) portion 1424, and an intermediate portion 1428 that are somewhat similar to the first portion 1320, the second portion 1324, and the intermediate portion 1328 illustrated and described above. Alternatively, the fusion implant 1412 can be designed without the intermediate portion 1428, and the first portion 1420 can be directly coextensive with the second portion 1424.

However, in this embodiment, the first portion 1420 of the implant body 1426 includes one or more first ridges 1430 having a helical design. Somewhat similarly, in this embodiment, the second portion 1424 of the implant body 1426 includes one or more second ridges 1432 having a helical design. With this design, the implant body 1426 can be effectively threaded into the first bone part 1214 and into the second bone part 1216.

Additionally, in some embodiments, the first ridges 1430 of the first portion 1420 can have a first pitch, and the second ridges 1432 of the second portion 1424 can have a second pitch that is different than the first pitch. By utilizing different pitches for the helical ridges 1430, 1432 in the first portion 1420 and the second portion 1424, respectively, the fusion implant 1412 is better able to draw the bone parts 1214, 1216 together as the fusion implant 1412 is inserted and implanted within the bone parts 1214, 1216.

Figure 15:
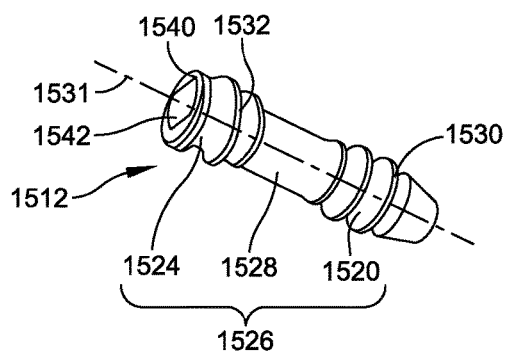
FIG. 15 is a perspective view of still another embodiment of a fusion implant having features of the present invention.

FIG. 15 is a perspective view of still another embodiment of a fusion implant 1512 having features of the present invention. As illustrated, the fusion implant 1512 is somewhat similar to the fusion implants 1312, 1412 illustrated and described above. In particular, in this embodiment, the fusion implant 1512 includes an implant body 1526 having a first (or leading) portion 1520, a second (or trailing) portion 1524, and an intermediate portion 1528 that are somewhat similar to the first portions 1320, 420, the second portions 1324, 1424, and the intermediate portions 1328, 1428 illustrated and described above. Alternatively, the fusion implant 1512 can be designed without the intermediate portion 1528, and the first portion 1520 can be directly coextensive with the second portion 1524.

However, in this embodiment, one of the portions 1520, 1524 of the implant body 1526 includes one or more ridges 1530, 1532 having a helical design, and the other portions 1520, 1524 of the implant body 1526 includes a plurality of spaced apart ridges 1530, 1532 that extend circumferentially substantially completely about the implant body 1526, i.e. that extend substantially transversely to a longitudinal axis 1531 of the implant body 1526. For example, in the embodiment shown in FIG. 15, (i) the first portion 1520 includes a plurality of spaced apart first ridges 1530 that extend circumferentially substantially completely about the implant body 1526 and substantially transversely to the longitudinal axis 1531 of the implant body 1526; and (ii) the second portion 1524 includes one or more second ridges 1532 having a helical design. Alternatively, the first portion 1520 can include one or more first ridges 1530 having a helical design; and the second portion 1524 can include a plurality of spaced apart second ridges 1532 that extend circumferentially substantially completely about the implant body 1526 and substantially transversely to the longitudinal axis 1531 of the implant body 1526.

Additionally, as illustrated in FIG. 15, an end 1540 of the implant body 1526, i.e. the end of the second portion 1524 of the implant body 1526, can have a driver recess 1542 that is adapted to receive and engage a portion of a driving tool (not illustrated). In particular, in one embodiment, the driver recess 1542 can have a substantially square-shaped cross-section that is adapted to receive and engage a substantially square-shaped portion of the driving tool. With this design, the rotation of the driving tool within the driver recess 1542 will result in rotation of the fusion implant 1512 and will enable the fusion implant 1512 to be effectively screwed into the bone parts 1214, 1216. Alternatively, the driver recess 1542 and the portion of the driving tool that engages the driver recess 1542 can have a different shape. Still alternatively, the fusion implant 1512 can be driven into the bone parts 1214, 1216 in a different manner and/or with a different driving tool.

Figure 16:
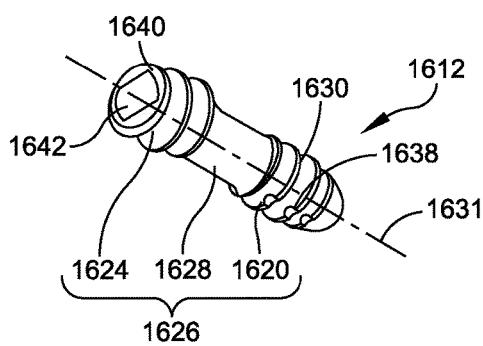
FIG. 16 is a perspective view of yet another embodiment of a fusion implant having features of the present invention.

FIG. 16 is a perspective view of yet another embodiment of a fusion implant 1612 having features of the present invention. As illustrated, the fusion implant 1612 is substantially similar to the fusion implant 1512 illustrated and described above in relation to FIG. 15. In particular, in this embodiment, the fusion implant 1612 includes an implant body 1626 having a first (or leading) portion 1620, a second (or trailing) portion 1624, and an intermediate portion 1628 that are substantially similar to the first portion 1520, the second portion 1524, and the intermediate portion 1528 illustrated and described above. As above, in an alternative embodiment, the fusion implant 1612 can be designed without the intermediate portion 1628, and the first portion 1620 can be directly coextensive with the second portion 1624.

However, in the embodiment illustrated in FIG. 16, the first portion 1620, which again includes a plurality of spaced apart first ridges 1630 that extend circumferentially substantially completely about the implant body 1626 and substantially transversely to a longitudinal axis 1631 of the implant body 1626, further includes a plurality of spaced apart longitudinal grooves 1638 or flutes that extend substantially perpendicularly to the first ridges 1630 in the first portion 1620. Moreover, the grooves 1638 extend substantially parallel to the longitudinal axis 1631 of the implant body 1626. As above, the grooves 1638 are provided to assist in the insertion of the fusion implant 1612 within the bone parts 1214, 1216 and/or to inhibit relative rotation between the first bone part 1214 and the second bone part 1216 after insertion of the fusion implant 1612.

Additionally, as shown in the embodiment illustrated in FIG. 16, an end 1640 of the implant body 1626, i.e. the end of the second portion 1624 of the implant body 1626, can again have a driver recess 1642 that is adapted to receive and engage a portion of a driving tool (not illustrated) to enable proper insertion and implanting of the fusion implant 1612 within the bone parts 1214, 1216.

Figure 17A:
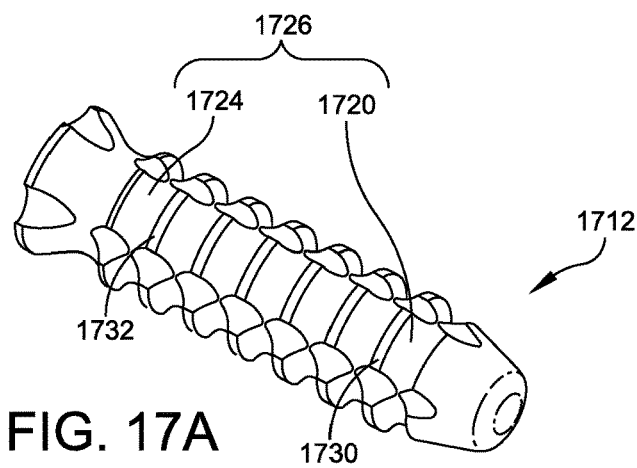
FIGS. 17A and 17B are alternative views of still another embodiment of a fusion implant having features of the present invention.
Figure 17B:
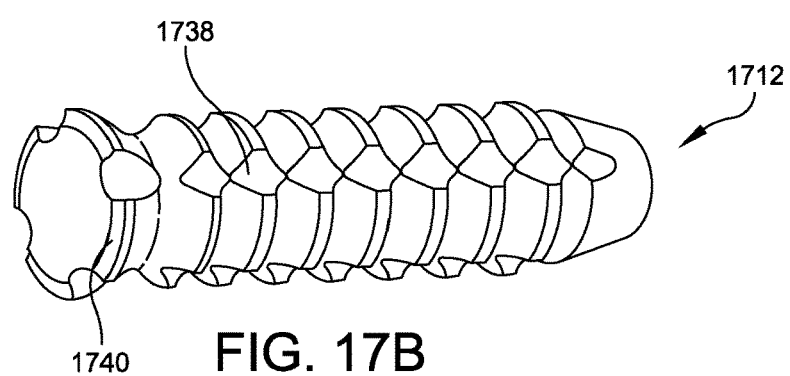

FIGS. 17A and 17B are alternative views of still another embodiment of a fusion implant 1712 having features of the present invention. As illustrated, the fusion implant 1712 is somewhat similar to the fusion implant 1312 illustrated and described above in relation to FIGS. 13A-13C. For example, in this embodiment, the fusion implant 1712 includes an implant body 1726, which has a first (or leading) portion 1720 and a second (or trailing) portion 1724, which is somewhat similar to the implant body 1326 illustrated and described above in relation to FIGS. 13A-13C. However, in this embodiment, the implant body 1726 is designed without an intermediate portion, and the first portion 1720 is directly coextensive with the second portion 1724.

Additionally, in the embodiment illustrated in FIGS. 17A and 17B, the first portion 1720 includes a plurality of spaced apart first ridges 1730 or teeth that extend circumferentially substantially completely about the implant body 1726; and the second portion 1724 includes a plurality of spaced apart second ridges 1732 or teeth that extend circumferentially substantially completely about the implant body 1726. As the first portion 1720 is directly coextensive with the second portion 1724, the first ridges 1730 and the second ridges 1732 cooperate to extend substantially the entire length of the implant body 1728.

In this embodiment, the implant body 1726 further includes a plurality of spaced apart longitudinal grooves 1738 or flutes that extend substantially perpendicularly to the ridges 1730, 1732 and extend substantially the entire length of the implant body 1726.

Figure 18A:
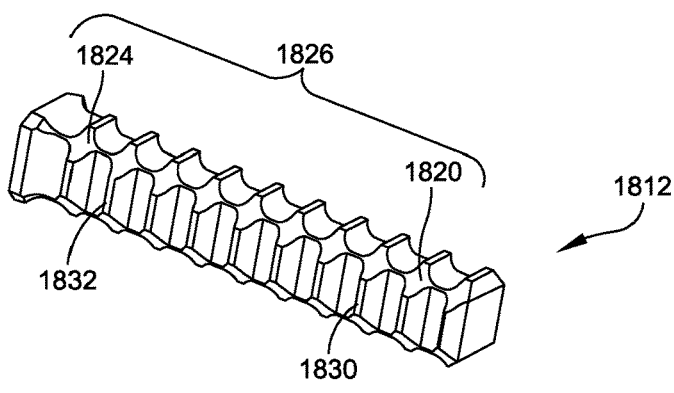
FIGS. 18A and 18B are alternative views of still yet another embodiment of a fusion implant having features of the present invention.
Figure 18B:
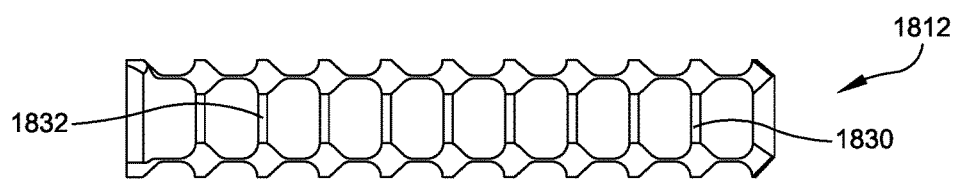

Moreover, as illustrated, the longitudinal grooves 1738 can extend fully to an end 1740 of the implant body 1726. With this design, the fusion implant 1712 can be driven into the bone parts 1214, 1216 with a driving tool (not illustrated) having tabs that engage with the grooves 1738 at or substantially near the end 1740 of the implant body 1726. Alternatively, the fusion implant 1712 can be driven into the bone parts 1214, 1216 in a different manner and/or with a different driving tool, FIGS. 18A and 18B are alternative views of still yet another embodiment of a fusion implant 1812 having features of the present invention. The fusion implant 1812 is somewhat similar to the previous embodiments. However, in this embodiment, the fusion implant 1812 includes an implant body 1826 having a first (or leading) portion 1820 and a second (or trailing) portion 1824 that each has a cross-section that is substantially hexagon-shaped.

Additionally, in one embodiment, the implant body 1826 can include a plurality of ridges or rings, i.e. a plurality of first ridges 1830 in the first portion 1820 and a plurality of second ridges 1832 in the second portion 1824, which extend circumferentially about the implant body 1826 along four of the six faces of the implant body 1826. Moreover, as illustrated, the first ridges 1830 and the second ridges 1832 can cooperate to extend substantially the entire length of the implant body 1826. Further, in one embodiment, the second portion 1824 can be somewhat larger than the first portion 1820 for improved compression as the fusion implant 1812 is implanted within the bone parts 1214, 1216.

Figure 19:
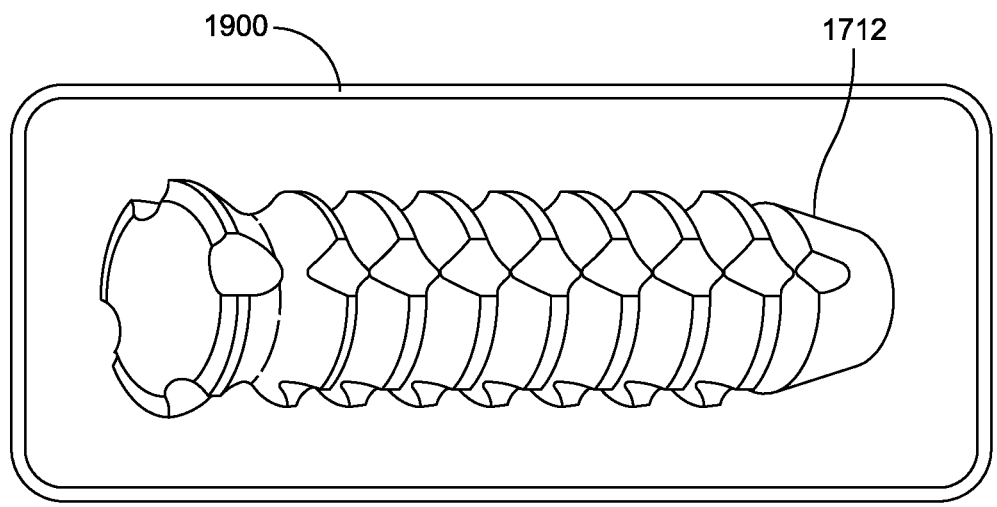
FIG. 19 illustrates a fusion implant of the invention in a sterile package.

In FIG. 19, fusion implant 1712 is illustrated in sterile package 1900. The implant 1712 is sterilized before sterile insertion into sterile package 1900. The sterile package is then sealed by conventional means known in the art. Alternatively, the implant 1712 can be inserted into the package 1900 followed by simultaneous sterilization of the package 1900 and implant 1712. Sterile packages of the type illustrated as 1900 can contain multiple implants and/or related tools and/or instruments.

While a number of exemplary aspects and embodiments of a fusion implant have been shown and disclosed herein above, those of skill in the art will recognize certain modifications, permutations, additions and sub-combinations thereof. It is therefore intended that the fusion implant shall be interpreted to include all such modifications, permutations, additions and sub-combinations as are within their true spirit and scope, and no limitations are intended to the details of construction or design herein shown.

What is claimed is:

1. An implant that is adapted to fuse a first bone part with a second bone part following a fracture or an osteotomy, the first bone part including a first receiving aperture, and the second bone part including a second receiving aperture, the implant comprising:

an implant body that is adapted to be inserted into and extend between the first bone part and the second bone part to hold the first bone part adjacent to the second bone part, the implant body including a first portion that is adapted to fit within the first receiving aperture in the first bone part, and a second portion that is adapted to fit within the second receiving aperture in the second bone part, wherein at least the second portion is formed to have a non-circular cross-sectional shape to inhibit relative motion between the bone parts and the implant body, the second portion having a longitudinal axis and a first plurality of ridges that are spaced apart along the longitudinal axis, and a cross-sectional shape at each of the ridges that is non-circular, and a second plurality of ridges spaced apart from the first plurality of ridges, wherein the first plurality of ridges is positioned on a first side surface of said implant body and said second plurality of ridges is positioned on a second side surface of said implant body, and wherein said second side surface is perpendicular to said first side surface.

2. The implant of claim 1 wherein the first portion has a circular or noncircular cross-sectional shape.

3. The implant of claim 1 wherein each of the first portion and the second portion are made of bone.

4. The implant of claim 1 wherein the second portion has a cross-sectional shape at each of the ridges that is triangular, square, rectangular, pentagonal, hexagonal or octagonal.

5. The implant of claim 1 wherein the first portion is threaded and includes a substantially circular cross-section that is threaded into the first receiving aperture.

6. The implant of claim 1 wherein at least one of the first portion and the second portion is made of cortical bone.

7. The implant of claim 1 wherein at least one of the first portion and the second portion is made of bone that is partially de mineralized.

8. The implant of claim 1 wherein the second portion of the implant body is a distal portion having a distal end and the first portion of the implant body is a proximal portion having a proximal end and the distal end has a recess adapted to cooperate with a driving tool.

9. The implant of claim 8 wherein the recess is in the shape of a square, a hexagon, a screwdriver slot or a phillips screwdriver slot.

10. The implant of claim 8, comprising an intermediate portion extending between the first portion and the second portion, wherein the intermediate portion is configured to extend substantially between the first bone part and the second bone part when the first portion is coupled to the first bone part and the second portion is coupled to the second bone part.

* * * * *